US009808626B2

(12) United States Patent
Libbus et al.

(10) Patent No.: US 9,808,626 B2
(45) Date of Patent: Nov. 7, 2017

(54) RESPONSIVE NEUROSTIMULATION FOR THE TREATMENT OF CHRONIC CARDIAC DYSFUNCTION

(71) Applicants: CYBERONICS, INC., Houston, TX (US); East Tennessee State University, Johnson City, TN (US)

(72) Inventors: Imad Libbus, St. Paul, MN (US); Badri Amurthur, Los Gatos, CA (US); Bruce H. KenKnight, Maple Grove, MN (US); Jeffrey L. Ardell, Johnson City, TN (US)

(73) Assignees: Cyberonics, Inc., Houston, TX (US); East Tennessee State University, Johnson City, TN (US)

( * ) Notice: Subject to any disclaimer, the term of this patent is extended or adjusted under 35 U.S.C. 154(b) by 0 days.

(21) Appl. No.: 15/267,922

(22) Filed: Sep. 16, 2016

(65) Prior Publication Data

US 2017/0001012 A1 Jan. 5, 2017

Related U.S. Application Data

(63) Continuation of application No. 14/861,390, filed on Sep. 22, 2015, now Pat. No. 9,446,237, which is a (Continued)

(51) Int. Cl.
*A61N 1/00* (2006.01)
*A61N 1/36* (2006.01)
*A61N 1/372* (2006.01)

(52) U.S. Cl.
CPC ........ *A61N 1/36114* (2013.01); *A61N 1/3615* (2013.01); *A61N 1/36053* (2013.01);
(Continued)

(58) Field of Classification Search
CPC .................................................... A61N 1/3605
(Continued)

(56) References Cited

U.S. PATENT DOCUMENTS 5,330,507 A 7/1994 Schwartz
5,522,854 A 6/1996 Ideker et al.
(Continued)

FOREIGN PATENT DOCUMENTS

WO WO-2013/086170 6/2013

OTHER PUBLICATIONS

US 8,315,702, 11/2012, Chavan et al. (withdrawn)
(Continued)

*Primary Examiner* — Nadia A Mahmood
(74) *Attorney, Agent, or Firm* — Foley & Lardner LLP

(57) ABSTRACT

Systems and methods are provided for delivering neurostimulation therapies to patients for treating chronic heart failure. A neural fulcrum zone is identified and ongoing neurostimulation therapy is delivered within the neural fulcrum zone. The implanted stimulation device includes a physiological sensor for monitoring the patient's response to the neurostimulation therapy on an ambulatory basis over extended periods of time and a control system for adjusting stimulation parameters to maintain stimulation in the neural fulcrum zone based on detected changes in the physiological response to stimulation.

20 Claims, 10 Drawing Sheets

Related U.S. Application Data continuation of application No. 14/271,714, filed on May 7, 2014, now Pat. No. 9,272,143.

(52) U.S. Cl.
CPC ..... *A61N 1/36135* (2013.01); *A61N 1/36139* (2013.01); *A61N 1/37217* (2013.01); *A61N 1/37264* (2013.01)

(58) Field of Classification Search
USPC .............................................. 607/2, 6, 9, 62
See application file for complete search history.

(56) References Cited

U.S. PATENT DOCUMENTS

| | | | |
|---|---|---|---|
| 5,707,400 A | 1/1998 | Terry, Jr. et al. |
| 5,928,272 A | 7/1999 | Adkins et al. |
| 5,978,709 A | 11/1999 | Begemann et al. |
| 6,006,134 A | 12/1999 | Hill et al. |
| 6,266,564 B1 | 7/2001 | Hill et al. |
| 6,354,991 B1 | 3/2002 | Gross et al. |
| 6,449,507 B1 | 9/2002 | Hill et al. |
| 6,473,644 B1 | 10/2002 | Terry et al. |
| 6,508,771 B1 | 1/2003 | Padmanabhan et al. |
| 6,522,926 B1 | 2/2003 | Kieval et al. |
| 6,600,954 B2 | 7/2003 | Cohen et al. |
| 6,610,713 B2 | 8/2003 | Tracey |
| 6,616,624 B1 | 9/2003 | Kieval |
| 6,622,041 B2 | 9/2003 | Terry, Jr. et al. |
| 6,652,449 B1 | 11/2003 | Gross et al. |
| 6,684,105 B2 | 1/2004 | Cohen et al. |
| 6,690,971 B2 | 2/2004 | Schauerte et al. |
| 6,712,772 B2 | 3/2004 | Cohen et al. |
| 6,718,208 B2 | 4/2004 | Hill et al. |
| 6,838,471 B2 | 1/2005 | Tracey |
| 6,839,594 B2 | 1/2005 | Cohen et al. |
| 6,850,801 B2 | 2/2005 | Kieval et al. |
| 6,862,480 B2 | 3/2005 | Cohen et al. |
| 6,892,098 B2 | 5/2005 | Ayal et al. |
| 6,896,651 B2 | 5/2005 | Gross et al. |
| 6,904,318 B2 | 6/2005 | Hill et al. |
| 6,907,295 B2 | 6/2005 | Gross et al. |
| 6,963,773 B2 | 11/2005 | Waltman et al. |
| 6,963,779 B1 | 11/2005 | Shankar |
| 6,985,774 B2 | 1/2006 | Kieval et al. |
| 7,010,345 B2 | 3/2006 | Hill et al. |
| 7,072,720 B2 | 7/2006 | Puskas |
| 7,123,961 B1 | 10/2006 | Kroll et al. |
| 7,136,705 B1 | 11/2006 | Park |
| 7,139,607 B1 | 11/2006 | Shelchuk |
| 7,158,832 B2 | 1/2007 | Kieval et al. |
| 7,184,828 B2 | 2/2007 | Hill et al. |
| 7,184,829 B2 | 2/2007 | Hill et al. |
| 7,189,204 B2 | 3/2007 | Ni et al. |
| 7,218,964 B2 | 5/2007 | Hill et al. |
| 7,221,979 B2 | 5/2007 | Zhou et al. |
| 7,225,017 B1 | 5/2007 | Shelchuk |
| 7,225,019 B2 | 5/2007 | Jahns et al. |
| 7,237,320 B2 | 7/2007 | Lam |
| 7,245,967 B1 | 7/2007 | Shelchuk |
| 7,260,431 B2 | 8/2007 | Libbus et al. |
| 7,269,457 B2 | 9/2007 | Shafer et al. |
| 7,277,761 B2 | 10/2007 | Shelchuk |
| 7,295,881 B2 | 11/2007 | Cohen et al. |
| 7,305,265 B2 | 12/2007 | Fukui |
| 7,321,793 B2 | 1/2008 | Ezra et al. |
| 7,324,853 B2 | 1/2008 | Ayal et al. |
| 7,336,997 B2 | 2/2008 | Fukui |
| 7,346,398 B2 | 3/2008 | Gross et al. |
| 7,387,603 B2 | 6/2008 | Gross et al. |
| 7,389,149 B2 | 6/2008 | Rossing et al. |
| 7,395,119 B2 | 7/2008 | Hagen et al. |
| 7,403,819 B1 | 7/2008 | Shelchuk et al. |
| 7,418,292 B2 | 8/2008 | Shafer |
| 7,452,800 B2 | 11/2008 | Sosnowchik et al. |
| 7,480,532 B2 | 1/2009 | Kieval et al. |
| 7,481,759 B2 | 1/2009 | Whitehurst et al. |
| 7,485,104 B2 | 2/2009 | Kieval |
| 7,493,167 B2 | 2/2009 | Hussein et al. |
| 7,499,742 B2 | 3/2009 | Bolea et al. |
| 7,499,747 B2 | 3/2009 | Kieval et al. |
| 7,499,748 B2 | 3/2009 | Moffitt et al. |
| 7,502,650 B2 | 3/2009 | Kieval |
| 7,542,800 B2 | 6/2009 | Libbus et al. |
| 7,548,780 B2 | 6/2009 | Libbus et al. |
| 7,551,958 B2 | 6/2009 | Libbus et al. |
| 7,561,922 B2 | 7/2009 | Cohen et al. |
| 7,561,923 B2 | 7/2009 | Libbus et al. |
| 7,570,999 B2 | 8/2009 | Libbus et al. |
| 7,582,053 B2 | 9/2009 | Gross et al. |
| 7,584,004 B2 | 9/2009 | Caparso et al. |
| 7,587,238 B2 | 9/2009 | Moffitt et al. |
| 7,606,622 B2 | 10/2009 | Reeve |
| 7,613,511 B2 | 11/2009 | Wu et al. |
| 7,613,516 B2 | 11/2009 | Cohen et al. |
| 7,616,990 B2 | 11/2009 | Chavan et al. |
| 7,617,003 B2 | 11/2009 | Caparso et al. |
| 7,623,926 B2 | 11/2009 | Rossing et al. |
| 7,627,384 B2 | 12/2009 | Ayal et al. |
| 7,628,750 B2 | 12/2009 | Cohen et al. |
| 7,630,760 B2 | 12/2009 | Libbus et al. |
| 7,634,315 B2 | 12/2009 | Cholette |
| 7,634,317 B2 | 12/2009 | Ben-David et al. |
| 7,640,057 B2 | 12/2009 | Libbus et al. |
| 7,647,101 B2 | 1/2010 | Libbus et al. |
| 7,647,114 B2 | 1/2010 | Libbus |
| 7,650,190 B2 | 1/2010 | Zhou et al. |
| 7,657,312 B2 | 2/2010 | Pastore et al. |
| 7,660,628 B2 | 2/2010 | Libbus et al. |
| 7,664,548 B2 | 2/2010 | Amurthur et al. |
| 7,668,602 B2 | 2/2010 | Ben-David et al. |
| 7,672,733 B2 | 3/2010 | Zhou et al. |
| 7,676,275 B1 | 3/2010 | Farazi et al. |
| 7,684,866 B2 | 3/2010 | Fowler et al. |
| 7,689,286 B2 | 3/2010 | Pastore et al. |
| 7,711,415 B1 | 5/2010 | Farazi et al. |
| 7,711,421 B2 | 5/2010 | Shafer et al. |
| 7,734,355 B2 | 6/2010 | Cohen et al. |
| 7,751,884 B2 | 7/2010 | Ternes et al. |
| 7,769,442 B2 | 8/2010 | Shafer |
| 7,769,446 B2 | 8/2010 | Moffitt et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,783,353 B2 | 8/2010 | Libbus et al. |
| 7,797,041 B2 | 9/2010 | Libbus et al. |
| 7,801,603 B2 | 9/2010 | Westlund et al. |
| 7,801,604 B2 | 9/2010 | Brockway et al. |
| 7,801,614 B2 | 9/2010 | Rossing et al. |
| 7,805,193 B2 | 9/2010 | Libbus et al. |
| 7,805,203 B2 | 9/2010 | Ben-David et al. |
| 7,813,805 B1 | 10/2010 | Farazi |
| 7,813,812 B2 | 10/2010 | Kieval et al. |
| 7,835,797 B2 | 11/2010 | Rossing et al. |
| 7,840,266 B2 | 11/2010 | Libbus et al. |
| 7,840,271 B2 | 11/2010 | Kieval et al. |
| 7,844,346 B2 | 11/2010 | Cohen et al. |
| 7,848,812 B2 | 12/2010 | Crowley et al. |
| 7,848,816 B1 | 12/2010 | Wenzel et al. |
| 7,869,869 B1 | 1/2011 | Farazi |
| 7,885,709 B2 | 2/2011 | Ben-David |
| 7,885,711 B2 | 2/2011 | Ben-Ezra et al. |
| 7,890,185 B2 | 2/2011 | Cohen et al. |
| 7,894,907 B2 | 2/2011 | Cowan et al. |
| 7,904,151 B2 | 3/2011 | Ben-David et al. |
| 7,904,175 B2 | 3/2011 | Scott et al. |
| 7,904,176 B2 | 3/2011 | Ben-Ezra et al. |
| 7,908,008 B2 | 3/2011 | Ben-David et al. |
| 7,916,013 B2 | 3/2011 | Stevenson |
| 7,925,342 B2 | 4/2011 | Amurthur et al. |
| 7,925,352 B2 | 4/2011 | Stack et al. |
| 7,974,693 B2 | 7/2011 | Ben-David et al. |
| 8,005,542 B2 | 8/2011 | Ben-Ezra et al. |
| 8,005,545 B2 | 8/2011 | Ben-David et al. |

(56) References Cited

U.S. PATENT DOCUMENTS

| | | | |
|---|---|---|---|
| 8,036,745 B2 | 10/2011 | Ben-David et al. | |
| 8,060,197 B2 | 11/2011 | Ben-David et al. | |
| 8,065,021 B2 | 11/2011 | Gross et al. | |
| 8,083,663 B2 | 12/2011 | Gross et al. | |
| 8,116,881 B2 | 2/2012 | Cohen et al. | |
| 8,131,362 B2 | 3/2012 | Moffitt et al. | |
| 8,160,701 B2 * | 4/2012 | Zhao | A61N 1/36114 607/9 |
| 8,160,705 B2 | 4/2012 | Stevenson et al. | |
| 8,195,290 B2 | 6/2012 | Brockway et al. | |
| 8,224,436 B2 | 7/2012 | Libbus et al. | |
| 8,249,711 B2 | 8/2012 | Libbus et al. | |
| 8,369,943 B2 | 2/2013 | Shuros et al. | |
| 8,386,038 B2 | 2/2013 | Bianchi et al. | |
| 8,401,640 B2 | 3/2013 | Zhao et al. | |
| 8,417,354 B2 | 4/2013 | Zhang et al. | |
| 8,571,654 B2 | 10/2013 | Libbus et al. | |
| 8,577,458 B1 | 11/2013 | Libbus et al. | |
| 8,600,505 B2 | 12/2013 | Libbus et al. | |
| 8,634,921 B2 | 1/2014 | Chavan et al. | |
| 8,688,212 B2 | 4/2014 | Libbus et al. | |
| 8,918,190 B2 | 12/2014 | Libbus et al. | |
| 8,923,964 B2 | 12/2014 | Libbus et al. | |
| 9,409,024 B2 | 8/2016 | Kenknight et al. | |
| 2002/0107553 A1 | 8/2002 | Hill et al. | |
| 2003/0040774 A1 | 2/2003 | Terry et al. | |
| 2003/0153954 A1 | 8/2003 | Park et al. | |
| 2003/0171781 A1 | 9/2003 | Florio et al. | |
| 2004/0199210 A1 | 10/2004 | Shelchuk | |
| 2004/0210261 A1 | 10/2004 | King et al. | |
| 2004/0215265 A1 | 10/2004 | Keizer | |
| 2005/0049655 A1 | 3/2005 | Boveja et al. | |
| 2005/0065553 A1 | 3/2005 | Ezra et al. | |
| 2005/0125044 A1 | 6/2005 | Tracey | |
| 2005/0131467 A1 | 6/2005 | Boveja | |
| 2005/0165465 A1 | 7/2005 | Pianca et al. | |
| 2005/0267542 A1 | 12/2005 | David et al. | |
| 2006/0015153 A1 | 1/2006 | Gliner et al. | |
| 2006/0100668 A1 | 5/2006 | Ben-David et al. | |
| 2006/0190053 A1 | 8/2006 | Dobak, III | |
| 2006/0206155 A1 | 9/2006 | Ben-David et al. | |
| 2006/0253161 A1 | 11/2006 | Libbus et al. | |
| 2007/0067004 A1 | 3/2007 | Boveja et al. | |
| 2007/0093870 A1 | 4/2007 | Maschino | |
| 2007/0179543 A1 | 8/2007 | Ben-David et al. | |
| 2007/0213773 A1 | 9/2007 | Hill et al. | |
| 2007/0233194 A1 | 10/2007 | Craig | |
| 2007/0255320 A1 | 11/2007 | Inman et al. | |
| 2007/0276453 A1 | 11/2007 | Hill et al. | |
| 2008/0015659 A1 | 1/2008 | Zhang et al. | |
| 2008/0021503 A1 | 1/2008 | Whitehurst et al. | |
| 2008/0033511 A1 | 2/2008 | Dobak | |
| 2008/0051839 A1 | 2/2008 | Libbus et al. | |
| 2008/0058874 A1 | 3/2008 | Westlund et al. | |
| 2008/0061240 A1 | 3/2008 | Heuft | |
| 2008/0091240 A1 | 4/2008 | Ben-David et al. | |
| 2008/0132983 A1 | 6/2008 | Cohen et al. | |
| 2008/0147140 A1 | 6/2008 | Ternes et al. | |
| 2008/0183258 A1 | 7/2008 | Inman | |
| 2008/0243196 A1 | 10/2008 | Libbus et al. | |
| 2008/0319513 A1 | 12/2008 | Pu et al. | |
| 2009/0024186 A1 | 1/2009 | Brockway et al. | |
| 2009/0030493 A1 | 1/2009 | Colborn et al. | |
| 2009/0118777 A1 | 5/2009 | Iki et al. | |
| 2009/0124848 A1 | 5/2009 | Miazga | |
| 2009/0149900 A1 | 6/2009 | Moffitt et al. | |
| 2009/0248097 A1 | 10/2009 | Tracey et al. | |
| 2009/0270953 A1 | 10/2009 | Ecker et al. | |
| 2009/0275956 A1 | 11/2009 | Burnes et al. | |
| 2010/0005482 A1 | 1/2010 | Mukker et al. | |
| 2010/0010556 A1 | 1/2010 | Zhao et al. | |
| 2010/0010603 A1 | 1/2010 | Ben-David et al. | |
| 2010/0016919 A1 | 1/2010 | Hill et al. | |
| 2010/0042173 A1 | 2/2010 | Farazi et al. | |
| 2010/0114197 A1 | 5/2010 | Burnes et al. | |
| 2010/0114203 A1 | 5/2010 | Burnes et al. |
| 2010/0114227 A1 | 5/2010 | Cholette et al. |
| 2010/0174341 A1 | 7/2010 | Bolea et al. |
| 2010/0286740 A1 | 11/2010 | Libbus et al. |
| 2010/0331908 A1 | 12/2010 | Farazi |
| 2011/0015692 A1 | 1/2011 | Libbus et al. |
| 2011/0082514 A1 | 4/2011 | Libbus et al. |
| 2011/0098796 A1 | 4/2011 | Ben-David et al. |
| 2011/0224749 A1 | 9/2011 | Ben-David et al. |
| 2011/0257708 A1 | 10/2011 | Kramer et al. |
| 2011/0313488 A1 | 12/2011 | Hincapie Ordonez et al. |
| 2012/0143286 A1 | 6/2012 | Hahn et al. |
| 2012/0172742 A1 | 7/2012 | Arcot-Krishnamurthy et al. |
| 2012/0185007 A1 | 7/2012 | Ziegler et al. |
| 2012/0185010 A1 | 7/2012 | Zhou et al. |
| 2012/0192874 A1 | 8/2012 | Bolea et al. |
| 2012/0271374 A1 | 10/2012 | Nelson et al. |
| 2012/0303080 A1 | 11/2012 | Ben-David et al. |
| 2013/0158616 A1 | 6/2013 | Libbus et al. |
| 2013/0158617 A1 | 6/2013 | Libbus et al. |
| 2013/0158618 A1 | 6/2013 | Libbus et al. |
| 2013/0238047 A1 | 9/2013 | Libbus et al. |
| 2013/0289646 A1 | 10/2013 | Libbus et al. |
| 2014/0025132 A1 | 1/2014 | Libbus et al. |
| 2014/0135862 A1 | 5/2014 | Libbus et al. |
| 2014/0135863 A1 | 5/2014 | Libbus et al. |
| 2014/0135864 A1 | 5/2014 | Libbus et al. |
| 2014/0228905 A1 | 8/2014 | Bolea |
| 2014/0277232 A1 | 9/2014 | Libbus et al. |
| 2015/0073511 A1 | 3/2015 | Libbus et al. |
| 2015/0073512 A1 | 3/2015 | Libbus et al. |
| 2015/0094962 A1 | 4/2015 | Hoegh et al. |
| 2015/0119956 A1 | 4/2015 | Libbus et al. |
| 2015/0119959 A1 | 4/2015 | Libbus et al. |
| 2015/0196762 A1 | 7/2015 | Amurthur et al. |
| 2015/0273214 A1 | 10/2015 | Kenknight et al. |
| 2015/0297894 A1 | 10/2015 | Kenknight et al. |
| 2015/0306394 A1 | 10/2015 | Libbus et al. |
| 2015/0306395 A1 | 10/2015 | Libbus et al. |
| 2015/0321001 A1 | 11/2015 | Libbus et al. |

OTHER PUBLICATIONS

Zhang, et al., "Chronic Vagus Nerve Stimulation Improves Autonomic Control and Attenuates Systemic Inflammation and Heart Failure Progression in a Canine High-Rate Pacing Model," Journal of the American Heart Association, Circ Heart Fail, 2, pp. 692-699 (2009).

Abraham, et al., "Devices in the management of advanced, chronic heart failure," Nature Reviews, vol. 10, pp. 98-110 (Feb. 2013) (Published online Dec. 11, 2012).

Adamson, et al., "Continuous Autonomic Assessment in Patients with Symptomatic Heart Failure: Prognostic Value of Heart Rate Variability Measured by an Implanted Cardiac Resynchronization Device," Circulation, Journal of the American Heart Association, 110, pp. 2389-2394 (2004).

Agostoni, et al., "Functional and Histological Studies of the Vagus Nerve and its Branches to the Heart, Lungs and Abdominal Viscera in the Cat," J. Physiol. 135, pp. 182-205 (1957).

Ajani, et al., "Prevalence of High C-Reactive Protein in Persons with Serum Lipid Concentrations within Recommended Values," Chemical Chemistry, 50:9, pp. 1618-1622 (2004).

Akiyama, et al., "Effects of right and left vagal stimulation on left ventricular acetylcholine levels in the cat," Acta Physiol Scand, 172, pp. 11-16 (2001).

Anand, et al., "C-Reactive Protein in Heart Failure: Prognostic Value and the Effect of Valsartan," Circulation, Journal of the American Heart Association, 112, pp. 1428-1434 (2005).

Anholt, et al., "Recruitment and blocking properties of the CardioFit stimulation lead," Journal of Neural Engineering, 8, pp. 1-6, (2011).

Ardell, et al.; "Selective vagal innervation of sinoatrial and atrioventricular nodes in canine heart," Am. J. Physiol. 251 (Heart Circ. Physiol. 20), pp. H764-H773 (1986).

Armour, "Cardiac neuronal hierarchy in health and disease," Am J Physiol Regul Integr Comp Physiol, 287, pp. R262-R271 (2004).

(56) References Cited

OTHER PUBLICATIONS

Armour, "Myocardial ischaemia and the cardiac nervous system," Cardiovascular Research, 41, pp. 41-54 (1999).
Armour, "The little brain on the heart," Cleveland Clinic Journal of Medicine, vol. 74, supp. 1, pp. S48-S51 (Feb. 2007).
Armour, et al., "Functional anatomy of canine cardiac nerves," Acta anat., 91, pp. 510-524 (1975).
Armour, et al., "Localized myocardial responses to stimulation of small cardiac branches of the vagus," American Journal of Physiology, vol. 228, No. 1 pp. 141-148 (Jan. 1975).
Armour, JA, "Potential clinical relevance of the 'little brain' on the mammalian heart," Experimental Physiology, vol. 1 93, No. 2, pp. 165-176 (Feb. 2008). Online Publication Date: Nov 2, 2007. Available at: http://ep.physoc.org/content/93/2/165.long.
Asala, et al., "An electron microscope study of vagus nerve composition in the ferret," Anat Embryol, 175, pp. 247-253 (1986).
Aukrust, et al., "Inflammatory and anti-inflammatory cytokines in chronic heart failure: Potential therapeutic implications," Annals of Medicine, 37, pp. 74-85 (2005).
Author Unknown, "Nerve fiber—Types and Function," www.boddunan.com Available at www.boddunan.com/education/20-medicine-a-surgery/12730-nerver-fiber- types-and-function.html (Apr. 19, 2010).
Author Unknown, American Diabetes Association, "Standards of Medical Care in Diabetes—2012," Diabetes Care, vol. 35, supplement 1, pp. S11-S63 (Jan. 2012).
Author Unknown, Staff of Adinstruments, "Principles of Nerve Stimulation," Application Note, ADInstruments (Apr. 2002).
Bae, et al., "Gliosis in the Amygdala Following Myocardial Infarction in the Rat," J Vet Med Sci, 72(8), pp. 1041-1045 (2010).
Bernik, et al., "Pharmacological Stimulation of the Cholinergic Antiinflammatory Pathway," J. Exp. Med, vol. 195, No. 6, pp. 781-788 (Mar. 18, 2002).
Berthoud, et al., "Functional and chemical anatomy of the afferent vagal system," Autonomic Neuroscience: Basic and Clinical, 85, pp. 1-17 (2000).
Bhagat, et al., "Differential Effect of Right and Left Vagal Stimulation on Right and Left Circumflex Coronary Arteries," S A Medical Journal, 50, pp. 1591-1594 (1976).
Biasucci, et al., "Elevated Levels of C-Reactive Protein at Discharge in Patients with Unstable Angina Predict Recurrent Instability," Circulation, Journal of the American Heart Association, 99, pp. 855-860 (1999).
Bibevski, et al., "Evidence for impaired vagus nerve activity in heart failure," Heart Fail Rev, 16, pp. 129-135 (2011).
Bibevski, et al., "Ganglionic Mechanisms Contribute to Diminished Vagal Control in Heart Failure," Circulation, Journal of the American Heart Association, 99, pp. 2958-2963 (1999).
Bilgutay, et al., "Vagal Tuning a new concept in the treatment of supraventricular arrhythmias, angina pectoris, and heart failure," Journal of Thoracic and Cardiovascular Surgery, vol. 56, No. 1, pp. 71-82 (Jul. 1968).
Binkley, et al., "Parasympathetic Withdrawal Is an Integral Component of Autonomic Imbalance in Congestive Heart Failure: Demonstration In Human Subjects and Verification In a Paced Canine Model Of Ventricular Failure," JACC, vol. 18, No. 2, pp. 464-472 (Aug. 1991).
Bois, et al., "Mode of action of bradycardic agent, S 16257, on ionic currents of rabbit sinoatrial node cells," Abstract, British Journal of Pharmacology, 118(4):1051-7 (1996).
Bonaz, et al., "Vagus nerve stimulation: From epilepsy to the cholinergic anti-inflammatory pathway," Neurogastroenterology & Motility, pp. 1-14 (2013).
Borggrefe, et al., "Vagal Stimulation Devices," ESC Congress 2010 (2010).
Borovilkova, et al., "Vagus nerve stimulation attenuates the systemic inflammatory response to endotoxin," Nature, vol. 405, pp. 458-462 (May 25, 2000).
Brack, et al., "Mechanisms underlying the autonomic modulation of ventricular fibrillation initiation—tentative prophylactic properties in vagus nerve stimulation on malignant arrhythmias in heart failure," Heart Fail Rev (Published online Jun. 8, 2012).
Bronzino, "Biomedical Engineering Fundamentals," CRC Press, Chapter 30, pp. 30-10-30-15 (Apr. 2006).
Buschman, et al., "Heart Rate Control Via Vagus Nerve Stimulation," Neuromodulation, vol. 9, No. 3, pp. 214-220 (2006).
Butterwick, et al., "Tissue Damage by Pulsed Electrical Stimulation," IEEE Transactions on Biomedical Engineering, vol. 54, No. 12, pp. 2261-2267 (Dec. 2007).
Calkins, et al., "Comparison of Responses to Isoproterenol and Epinephrine During Head-Up Tilt in Suspected Vasodepressor Syncope," The American Journal of Cardiology, vol. 67 pp. 207-209 (Jan. 15, 1991).
Castoro et al., "Excitation properties of the right cervical vagus nerve in adult dogs," Experimental Neurology, vol. 2 227, iss. 1, pp. 62-68 (Jan. 2011). Online Publication Date: Sep. 17, 2010. Available at: http://www.sciencedirecl.com/science/article/pii/SOO1448861000347X.
Chapleau, et al., "Methods of assessing vagus nerve activity and reflexes," Heart Fail Rev, 16, pp. 109-127 (2011).
Chen, et al., "National and Regional Trends in Heart Failure Hospitalization and Mortality Rates for Medicare Beneficiaries, 1998-2008," JAMA, vol. 306, No. 15 (Oct. 19, 2011).
Chen, et al., "Role of Atrial Electrophysiology and Autonomic Nervous System in Patients with Supraventricular Tachycardia and Paroxysmal Artrial Fibrillation," J Am Coll Cardiol, vol. 32, No. 3, pp. 732-738 (Sep. 1998).
Cheng, et al., "Long-term Outcomes in Individuals with Prolonged PR Interval or First-Degree Atrioventricular Block," JAMA, vol. 301, No. 24 pp. 2571-2577 (Jun. 24, 2009).
Chiou, et al., "Effects of Continuous Enhanced Vagal Tone and Dual Atrioventricular Node and Accessory Pathways," Circulation, Journal of the American Heart Association, 107, pp. 2583-2588 (2003).
Cohen, et al., "Histopathology of the stimulated Vagus nerve: Primum non nocere," Heart Fail Rev, 16, pp. 163-169 (2011).
Colombo, et al., "Comparison between spectral analysis and the phenylephrine methods for the assessment of baroreflex sensitivity in chronic heart failure," Clinical Science, 97, pp. 503-513 (1999).
Cryan, et al., "Animal models and mood disorders: recent developments," Current Opinion in Psychiatry, 20, pp. 1-7 (2007).
Das, "Vagal nerve stimulation in prevention and management of coronary heart disease," World J. Cardiol, 3(4), pp. 105-110 (Apr. 26, 2011).
De Castro, et al., "Parasympathetic-mediated atrial fibrillation during tilt test associated with increased baroreflex sensitivity," The European Society of Cardiology, Europace, 8, pp. 349-351 (2006).
De Ferrari et al., Chronic Vagus Nerve Stimulation: A New and Promising Therapeutic Approach for Chronic Heart Failure, European Heart Journal, vol. 32, Oct. 28, 2010, pp. 847-855.
De Ferrari, et al., "Baroreflex Sensitivity Predicts Long-Term Cardiovascular Mortality After Myocardial Infarction Even in Patients with Preserved Left Ventricular Function," Journal of the American College of Cardiology, vol. 50, No. 24, pp. 2285-2290 (2007).
De Ferrari, et al., "Chronic Vagal Stimulation in Patients with Congestive Heart Failure," 31st Annual International Conference of the IEE EMBS (2009).
De Ferrari, et al., "Vagus nerve stimulation: from pre-clinical to clinical application: challenges and future directions," Heart Fail Rev, 16, pp. 195-203 (2011) (Published Online Dec. 17, 2010).
De Jonge, et al., "Stimulation of the vagus nerve attenuates macrophage activation by activating the Jak2-STAT3 signaling pathway," Nature Immunology, vol. 6, No. 8, pp. 844-852 (Aug. 2005).
Desai, et al., "Pharmacologic modulation of parasympathetic activity in heart failure," Heart Fail Rev, 16, pp. 179-193 (Published online: Oct. 6, 2010) (2011).
Dickerson, et al., "Parasympathetic neurons in the cranial medial ventricular fat pad on the dog heart selectively decrease ventricular contractility," Journal of the Autonomic Nervous System, 70, pp. 129-141 (1998).
Dunlap, et al., "Mechanisms of altered vagal control in heart failure: influence of muscarinic receptors and acetylcholinesterase activity," Am J Physiol Heart Gire Physiol, 285, pp. H1632-H1640 (Jun. 26, 2003).

(56) References Cited

OTHER PUBLICATIONS

Elsenbruch, et al., "Heart Rate Variability During Waking and Sleep in Healthy Males and Females," SLEEP, vol. 22, No. 8, pp. 1067-1071 (1999).
Euler, et al., "Acetylcholine release by a stimulus train lowers atrial fibrillation threshold," Am. J Physiol. 253 (Heart Gire. Physiol, 22), pp. H863-H868 (1987).
Evans, et al., "Histological and functional studies on the fibre composition of the vagus nerve of the rabbit," Journal of Anatomy, 130, pp. 139-151 (1954).
Fallen, "Vagal Afferent Stimulation as a Cardioprotective Strategy? Introducing the Concept," A.N.E., vol. 10, No. 4 (Oct. 2005).
Fan, et al., "Transvenous vagus nerve stimulation: A potential heart failure therapy is feasible in humans," JACC, vol. 55, issue 10A, pp. E152-E153 (2010).
Fazan, et al., "Diabetic Peripheral Neuropathies: A Morphometric Overview," Int. J. Morphol, 28(I), pp. 51-64 (2010).
Feinauer, et al., "Ouabain enhances release of acetylcholine in the heart evoked by unilateral vagal stimulation," Arch Pharmacol, 333, pp. 7-12 (1986).
Fonarow, et al., "Incremental Reduction in Risk of Death Associated with Use of Guideline-Recommended Therapies in Patients with Heart Failure: A Nested Case-Control Analysis of IMPROVE HF," J Am Heart Assoc, 1, pp. 16-26 (2012).
Ford, et al., "The effects of electrical stimulation of myelinated and non-myelinated vagal fibres on heart rate in the rabbit," J. Physiol. 380, pp. 341-347 (1986).
Furukawa, et al., "Effects of Verapamil, Zatebradine, and E-4031 on the Pacemaker Location and Rate in Response to Sympathetic Stimulation in Dog Hearts," The Journal of Pharmacology and Experimental Therapeutics, vol. 289, No. 3, pp. 1334-1342 (1999).
Furukawa, et al., "Selective inhibition by zatebradine and discrete parasympathetic stimulation of the positive chronotropic response to sympathetic stimulation in anesthetized dogs," Abstract, Journal of Pharmacology & Experimental Therapeutics, 272(2):744-9 (1995).
Gatti, et al., "Can neurons in the nucleus ambiguous selectively regulate cardiac rate and atrio-ventricular conduction?" Journal of the Autonomic Nervous System, 57, pp. 123-127 (1996).
Gatti, et al., "Vagal control of left ventricular contractility is selectively mediated by a cranioventricular intracardiac ganglion in the cat," Journal of the Autonomic Nervous System, 66, pp. 138-144 (1997).
Gibbons, et al., "Neuromodulation targets intrinsic cardiac neurons to attenuate neuronally mediated atrial arrhythmias," Am J Physiol Regul Integr Comp Physiol 302: R357-R364 (2012) (First published Nov. 16, 2011).
Gottdiener, et al., "Predictors of Congestive Heart Failure in the Elderly: The Cardiovascular Health Study," Journal of the American College of Cardiology, vol. 35, No. 6, pp. 1628-1637 (2000).
Gray, et al., "Parasympathetic control of the Heart. II. A novel interganglionic intrinsic cardiac circuit mediates neural control of heart rate," J. Appl Physiol, 96, pp. 2273-2278 (2004).
Gray, et al., "Parasympathetic control of the Heart. III. Neuropeptide Y- immunoreactive nerve terminals synapse on three populations of negative chronotropic vagal preganglionic neurons," J. Appl Physiol, 96, pp. 2279-2287 (2004).
Grill, "Chapter 14—Principles of Electric Field Generation for Stimulation of the Central Nervous System," Neuromodulation, Academic Press (2009).
Guilleminault, et al., "Cyclical Variation of the Heart Rate in Sleep Apnea Syndrome," The Lancet, pp. 126-131 (Jan. 21, 1984).
Hardwick, et al., "Chronic myocardial infarction induces phenotypic and functional remodeling in the guinea pig cardiac plexus," Am J Physiol Regulatory Integrative Comp Physiol, 295, pp. 1926-1933 (2008).
Hardwick, et al., "Remodeling of the guinea pig intrinsic cardiac plexus with chronic pressure overload," Am J Physiol Regulatory Integrative Comp Physiol, 297, pp. 859-866 (2009).
Hauptman, et al., "The vagus nerve and autonomic imbalance in heart failure: past, present, and future," Heart Fail Rev, 16, pp. 97-99 (2011).
Hellyer, et al., "Autonomic nerve activity and blood pressure in ambulatory dogs," Heart Rhythym, vol. 11(2), pp. 307-313 (Feb. 2014).
Hirooka, et al., "Imbalance of central nitric oxide and reactive oxygen species in the regulation of sympathetic activity and neural mechanisms of hypertension," Am J Physiol Regulatory Integration Comp Physiol, 300, pp. 818-826 (2011).
Hoffman, et al., "Vagus Nerve Components," Anat Rec, 127, pp. 551-568 (1957).
Hu, et al., "Role of sympathetic nervous system in myocardial ischemia injury: Beneficial or deleterious?" Letters to the Editor, Elsevier Ireland Ltd. (Mar. 27, 2012).
Hua, et al., "Left vagal stimulation induces dynorphin release and suppresses substance P release from the rat thoracic spinal cord during cardiac ischemia," Am J Physiol Regulatory Integration Comp Physiol, 287, pp. 1468-1477 (2004).
Huston, et al., "Splenectomy inactivates the cholinergic antiinflammatory pathway during lethal endotoxemia and polymicrobial sepsis," J. Exp. Med, vol. 203, No. 7 pp. 1623-1628 (Jun. 19, 2006).
Huston, et al., "Transcutaneous vagus nerve stimulation reduces serum high mobility group box 1 levels and improves survival in murine sepsis," Grit Care Med, vol. 35, No. 12, pp. 2762-2768 (2007).
Ingemansson, et al., "Autonomic modulation of the atrial cycle length by the head up tilt test: non-invasive evaluation in patients with chronic atrial fibrillation," Heart, 80, pp. 71-76 (1998).
Ito, et al., "Efferent sympathetic and vagal innervation of the canine right ventricle," Circulation, Journal of the American Heart Association, vol. 90, pp. 1469-1468 (1994).
Jacques, et al., "Spinal Cord Stimulation Causes Potentiation of Right Vagus Nerve Effects on Atrial Chronotropic Function and Repolarization in Canines," Journal of Cardiovascular Electrophysiology, vol. 22, No. 4, pp. 440-447 (Apr. 2011).
Jaenisch, et al., "Respiratory muscle training improves baroreceptor sensitivity, decrease sympathetic tonus and increase vagal effect in rats with heart failure," European Heart Journal, 32 (Abstract Supplement, pp. 976 (2011).
Jammes, et al., "Afferent and efferent components of the bronchial vagal branches in cats," Journal of the Autonomic Nervous System, 5, pp. 165-176 (1982).
Janabi, et al., "Oxidized LDL-Induced NF-kB Activation and Subsequent Expression of Proinflammatory Genes are Defective in Monocyte-Derived Macrophages from CD36-Deficient Patients," Arterioscler Thromb Vase Biol., 20:1953-1960 (2000).
Janse, et al., "Effects of unilateral stellate ganglion stimulation and ablation on electrophysiologic changes induced by acute myocardial ischemia in dogs," Circulation, Journal of the American Heart Association, 72, pp. 585-595 (1985).
Jessup; et al., "2009 Focused Update: ACCF/AHA Guidelines for the Diagnosis and Management of Heart Failure in Adults," Circulation, Journal of the American Heart Association, vol. 119, pp. 1977-2016 (2009).
Johnson, et al., "Parasympathetic control of the heart. I. An interventriculo-septal ganglion is the major source of the vagal intracardiac innervation of the ventricles," J Appl Physiol, 96, pp. 2265-2272 (2004).
Kakinuma, et al., "Cholinoceptive and cholinergic properties of cardiomyocytes involving an amplification mechanism for vagal efferent effects in sparsely innervated ventricular myocardium," FEBS Journal, 276, pp. 5111-5125 (2009).
Kalman, "Specific effects of zatebradine on sinus node function: suppression of automaticity, prolongation of sinoatrial conduction and pacemaker shift in the denervated canine heart," Abstract, Journal of Pharmacology & Experimental Therapeutics, 272(1):85-93 (1995).
Kaneko, et al., "C-Reactive Protein in Dilated Cardiomyopathy," Cardiology, 91, pp. 215-219 (1999).
Katare, et al., "Vagal nerve stimulation prevents reperfusion injury through inhibition of opening of mitochondrial permeability tran-

(56) References Cited

OTHER PUBLICATIONS sition pore independent of bradycardiac effect," The Journal of Thoracic and Cardiovascular Surgery, vol. 137, No. 1, pp. 223-231 (2009).
Katz, et al., "Diseases of the heart in the Works of Hippocrates," Br Heart J, 24, pp. 257-264 (1962).
Kawada, et al., "High-frequency dominant depression of peripheral vagal control of heart rate in rats with chronic heart failure," Acta Physiol 207, 494-502 (2013).
Kawada, et al., "Vagal stimulation suppresses isschemia-induced myocardial interstitial norepinephrine release," Life Sciences, 78, pp. 882-887 (2006).
Kawashima, "The autonomic nervous system of the human heart with special reference to its origin, course, and peripheral distribution," Anat Embryol, 209, pp. 425-438 (2005).
Klein et al., "Vagus nerve stimulation: A new approach to reduce heart failure," Cardiology Journal, vol. 17, iss. 6, pp. 638-643 (2010).
Kliks, et al., "Influence of Sympathetic Tone on Ventricular Fibrillation Threshold During Experimental Coronary Occlusion," The American Journal of Cardiology, vol. 36, pp. 45-49 (Jul. 1975).
Kolman, et al., "The effect of vagus nerve stimulation upon vulnerability of the canine ventricle: role of sympathetic-parasympathetic interactions," Journal of the American Heart Association, 52, pp. 578-585 (1975).
Kong, et al., "Optimizing the Parameters of Vagus Nerve Stimulation by Uniform Design in Rats with Acute Myocardial Infarction," PLOS One, vol. 7, issue 11 (Nov. 2012).
Koopman, et al., "Pilot study of stimulation of the cholinergic anti-inflammatory pathway with an implantable vagus nerve stimulation device in patients with rheumatoid arthritis," Abstract (2012).
Kulbertus, et al., ed., "Neurocardiology," Futura Publishing Co., pp. 13 ("Anatomy of the Cardiac Efferent Innvervation"); 61-63 ("Autonomic Neural Control"); 87, 89, 9293 ("Sympathetic-Parasympathetic Interactions"); 183, 187 ("Parasympathetic Nervous System"); 104 (1988).
La Rovere, et al., "Baroreflex sensitivity and heart-rate variability in prediction of total cardiac mortality after myocardial infarction. ATRAMI (Autonomic Tone and Reflexes After Myocardial Infarction) Investigators," Lancet, 351(9101), pp. 478-84 (Feb. 14, 1998).
Lane, et al., "Prediction and Prevention of Sudden Cardiac Death in Heart Failure," Heart, 91, pp. 674-680 (2005).
Lechat, et al., "Heart rate and Cardiac Rhythm Relationships with Bisoprolol Benefit in Chronic Heart Failure in CIBIS II Trial," Circulation, Journal of American Heart Association, 103, pp. 1428-1433 (2001).
Lewis, et al., "Vagus nerve stimulation decreases left ventricular contractility in vivo in the human and pig heart," Journal of Physiology, 534, pp. 547-552 (2001).
Li et al., "Vagal Nerve Stimulation Markedly Improves Long-Term Survival After Chronic Heart Failure in Rats," Circulation: Journal of the American Heart Association, vol. 109, iss. 1, pp. 120-124 (Jan. 2004). Online publication date: Dec. 8, 2003.
Li, et al., "Early vagal stimulation markedly prevented cardiac dysfunction in rats after acute myocardial infarction in addition to suppressing arrhythmic death," European Heart Journal, 32 (Abstract Supplement), pp. 297-298 (2011).
Li, et al., "Inflammatory cytokines and nitric oxide in heart failure and potential modulation by vagus nerve stimulation," Heart Fail Rev, 16, pp. 137-145 (2011).
Li, et al., "Low-Level Vagosympathetic Stimulation. A Paradox and Potential New Modality for the Treatment of Focal Atrial Fibrillation," Gire Arrhythm Electrophysiol, Journal of American Heart Association, 2, pp. 645-651 (2009).
Li, et al., "Restoration of vagal tone by donepezil, on top of losartan treatment, markedly suppresses ventricular dysfunction and improves long-term survival in chronic heart failure rats," European Heart Journal, 32 (Abstract Supplement), pp. 642 (2011).
Libby, et al., "Inflammation and Atherosclerosis," Circulation, Journal of the American Heart Association, 105, pp. 1135-1143 (2002).

Liu, et al., "Differing sympathetic and vagal effects on atrial fibrillation in dogs: role of refractoriness heterogeneity," Am. J. Physiol. 273 (Heart Gire. Physiol. 42), pp. H805-H816 (1997).
Lo, et al., "Paradoxical long-term proarrhythmic effects after ablating the 'head station' ganglionated plexi of the vagal innervation to the heart," Heart Rhythm, vol. 10, No. 5, pp. 751-757 (May 2013).
Lohmeier, et al., "Prolonged Activation of the Barorelfex Produces Sustained Hypotension," Hypertension, Journal of the American Heart Association, 43, pp. 306-311 (2004).
Lu, et al., "Vagal nerve stimulation produces cardiac injury by attenuating mitochondrial dysfunction in a murine burn injury model," J. Cell. Mol. Med., vol. 17, No. 5, pp. 664-671 (2013).
Ma, et al., "Analysis of afferent, central, and efferent components of the baroreceptor reflex in mice," Am J Physiol Regulatory Integration Comp Physiol, 283, pp. 1033-1040 (2002).
Maj, et al., "P5775: Autonomic imbalance and circulating androgens and estrogens in men with systolic heart failure," European Heart Journal, 32 (Abstract Supplement), pp. 1090 (2011).
Malkin, et al., "Life-saving or life-prolonging? Interpreting trial data and survival curves for patients with congestive heart failure," The European Journal of Heart Failure, 7, pp. 143-148 (2005).
Mann, "Chapter 12—Peripheral Nerves," The Nervous System in Action, michaeldmann.net/mannI2.html, (Jul. 2011).
Mann, "Inflammatory Mediators and the Failing Heart. Past, Present, and the Foreseeable Future," Circ Res., 91, pp. 988-998 (2002).
Mann, "Stress-Activated Cytokines and the Heart: From Adaptation to Maladaptation," Annu. Rev. Physiol., 65, pp. 81-101 (2003).
Martin-Portugues, et al., "Histopathologic features of the vagus nerve after electrical stimulation in swine," Histol Histopathol, 20, pp. 851-856 (2005).
Martins, et al., "Distribution of Local Repolarization Changes Produced by Efferent Vagal Stimulation in the Canine Ventricles," JACC, vol. 2, No. 6, pp. 1191-1199 (Dec. 1983).
Massari, et al., "Neural control of left ventricular contractility in the dog heart: synaptic interactions of negative inotropic vagal preganglionic neurons in the nucleus ambiguus and tyrosine hydroxylase immunoreactive terminals," Brain Research, 802, pp. 205-220 (1998).
May, et al., "P564: Long-term prediction of all-cause mortality in diabetic autonomic neuropathy: simple function tests or 24-hour heart rate variability (HRV)?" European Heart Journal, 32 (Abstract Supplement, pp. 64 (2011).
Mei, et al., "The Composition of the Vagus Nerve of the Cat," Cell Tissue Res., 209, pp. 423-431 (1980).
Merrill, et al., "Electrical stimulation of excitable tissue: design of efficacious and safe protocols," Journal of Neuroscience Methods, 141, pp. 171-198 (2005).
Mortara, et al., "Arterial Baroreflex Modulation of Heart Rate in Chronic Heart Failure," Circulation, Journal of the American Heart Association, vol. 96, No. 10, pp. 3450-3458 (Nov. 18, 1997).
Murakawa, et al., "Effect of Cervical Vagal Nerve Stimulation on Defibrillation Energy," Jpn Heart J, 44, pp. 91-100 (Jan. 2003).
Naito, "Effects of zatebradine and propranolol on canine ischemia and reperfusion-induced arrhythmias," European Journal of Pharmacology, 388, pp. 171-176 (2000).
Nakajima, et al., "Autonomic Control of the Location and Rate of the Cardiac Pacemaker in the Sinoatrial Fat Pad of Parasympathetically Denervated Dog Hearts," Journal of Cardiovascular Electrophysiology, vol. 13, No. 9 pp. 896-901 (Sep. 2002).
Nearing, et al., "Crescendo in Depolarization and Repolarization Heterogeneity Heralds Development of Ventricular Tachycardia in Hospitalized Patients with Decompensated Heart Failure," Circulation Arrhythmia and Electrophysiology, Journal of the American Heart Association, 5, pp. 84-90 (2012).
Nihei, et al., "Decreased Vagal Control Over Heart Rate in Rats with Right-Sided Congestive Heart Failure—Downregulation of Neuronal Nitric Oxide Synthase," Gire J, 69, pp. 493-499 (2005).
Ninomiya, "Direct Evidence of Nonuniform Distribution of Vagal Effects on Dog Atria," Circulation Research, vol. XIX, pp. 576-583 (Sep. 1966).
Nolan, et al., "Prospective Study of Heart Rate Variability and Mortality in Chronic Heart Failure: Results of the United Kingdom

(56) References Cited

OTHER PUBLICATIONS

Heart Failure Evaluation and Assessment of Risk Trial (UK-Heart)," Circulation, Journal of the American Heart Association, 98, pp. 1510-1516 (1998).
Ochoa, et al., "P2497: Effects of insulin resistance on resting heart rate, baroreflex sensitivity and indices of autonomic cardiovascular modulation in individuals with high blood pressure levels," European Heart Journal, 32 (Abstract Supplement, pp. 431-432 (2011).
Ogawa, et al., "Left Stellate Ganglion and Vagal Nerve Activity and Cardiac Arrhythmias in Ambulatory Dogs with Pacing-Induced Congestive Heart Failure," Journal of the American College of Cardiology, vol. 50, No. 4, pp. 335-444 (2007).
Okada, et al., "Cyclic Stretch Upregulates Production of Interleukin-8 and Monocyte Chemotactic and Activating Factor/Monocyte Chemoattractant Protein-1 in Human Endothelial Cells," Arterioscler Thromb Vase Biol., 18, pp. 894-901 (1998).
Oliveira, et al., "Effects of vagal stimulation on induction and termination of atrial fibrillation in an in vivo rabbit heart model," Rev Port Cardiol, 29(03), pp. 375-389 (2010).
Olshansky, et al., "Parasympathetic Nervous System and Heart Failure: Pathophysiology and Potential Implications for Therapy," Circulation, Journal of the American Heart Association, 118, pp. 863-871 (2008).
Onkka, et al., "Sympathetic nerve fibers and ganglia in canine cervical vagus nerves: Localization and quantitation," Heart Rhythm, vol. 10, No. 4, pp. 585-591 (Apr. 2013).
Ordelman, et al., "Selectivity for Specific Cardiovascular Effects of Vagal Nerve Stimulation with a Multi-Contact Electrode Cuff," IEEE, pp. 1-6 (2011).
Packer, et al., "Effect of Carvedilol on Survival in Severe Chronic Heart Failure," The New England Journal of Medicine, vol. 344, No. 22, pp. 1651-1658 (May 31, 2001).
Pavlov, et al., "Central muscarinic cholinergic regulation of the systemic inflammatory response during endotoxemia," PNAS, vol. 103, No. 13, pp. 5219-5223 (Mar. 28, 2006).
Pavlov, et al., "Controlling inflammation: the cholinergic anti-inflammatory pathway," Biochemical Society Transactions, vol. 34, part 6, pp. 1037-1040 (2006).
PCT Application No. PCT/US2012/068205, Search Report and Written Opinion dated Feb. 8, 2013, 15 pages.
PCT Application No. PCT/US2012/068211, Search Report and Written Opinion dated Jun. 13, 2013.
PCT Application No. PCT/US2012/068213, Search Report and Written Opinion dated Mar. 15, 2013, 11 pages.
PCT Application No. PCT/US2012/068223, Search Report and Written Opinion dated Apr. 3, 2013, 11 pages.
PCT Application No. PCT/US2013/021964, Search Report and Written Opinion dated Jul. 25, 2013, 9 pages.
PCT Application No. PCT/US2013/050390, Search Report and Written Opinion dated Nov. 5, 2013.
PCT Application No. PCT/US2013/068541, International Preliminary Report on Patentability dated May 21, 2015, 9 pages.
PCT Application No. PCT/US2014/024827, Search Report and Written Opinion dated Nov. 11, 2014, 18 pages.
PCT Application No. PCT/US2015/020116, Search Report and Written Opinion dated Jul. 6, 2015, 12 pages.
Peckham, et al., "Chapter 18—Implantable Neural Stimulators," Neuromodulation, Academic Press (2009).
Pina, et al., "The Predictive Value of Biomarkers in Heart Failure," Medscape Education Cardiology, Available at http://www.medscape.org/viewarticle/765328 (CME Released: Jun. 15, 2012).
Pitzalis, et al., "Comparison Between Noninvasive Indices of Baroreceptor Sensitivity and the Phenylephrine Method in Post-Myocardial Infarction Patients," Circulation, Journal of the American Heart Association, 97, pp. 1362-1367 (1998).
Poole-Wilson, "Relation of Pathophysiologic Mechanisms to Outcome in Heart Failure," JACC, vol. 22, No. 4 (supplement A), pp. 22A-29A (Oct. 1993).
Pye, et al., "Study of serum C-reactive protein concentration in cardiac failure," Br Heart J, 63, pp. 228-230 (1990).
Rademacher, et al., "P5878: Multidimensional halter-based analysis of cardiac autonomic regulation predicts early AF recurrence after electrical cardioversion," European Heart Journal, 32 (Abstract Supplement), pp. 1116-1117 (2011).
Randall, et al., "Regional vagosympathetic control of the heart," American Journal of Physiology, vol. 227, No. 2, pp. 444-452 (1974).
Randall, et al., "Selective Vagal Innervation of the Heart," Annals of Clinical and Laboratory Science, vol. 16, No. 3, pp. 198-208 (1986).
Raymond, et al., "Elevated interleukin-6 levels in patients with asymptomatic left ventricular systolic dysfunction," American Heart Journal, vol. 141, No. 3, pp. 435-438 (Mar. 2001).
Rhee, et al., "Effects of suprathreshold vagal stimulation on stellate ganglion nerve activity in ambulatory dogs," 33rd Annual Scientific Sessions, Heart Rhythm, Presentation Abstract (2012).
Riccio, et al., "Interganglionic segregation of distinct vagal afferent fibre phenotypes in guinea-pig airways," Journal of Physiology, 495.2, pp. 521-530 (1996).
Riddle, et al., "Epidemiologic Relationships Between A1C and All-Cause Mortality During a Median 3.4-Year Follow-up of Glycemic Treatment in the ACCORD Trial," Diabetes Care, vol. 33, No. 5, pp. 983-990 (May 2010).
Ridker, C-Reactive Protein: A Simple Test to Help Predict Risk of Heart Attack and Stroke, Journal of the American Heart Association, 108, pp. e81-e85 (2003).
Ridker, et al., "Comparison of C-Reactive Protein and Low-Density Lipoprotein Cholesterol Levels in the Prediction of First cardiovascular Events," New England Journal of Medicine, vol. 347, No. 20, pp. 1557-1566 (Nov. 14, 2002).
Ridker, et al., "C-Reactive Protein and Other Markers of Inflammation in the Prediction of Cardiovascular Disease in Women," The New England Journal of Medicine, vol. 342, No. 12, pp. 836-841 (Mar. 23, 2000).
Ridker, et al., "Inflammation, Pravastatin, and the Risk of Coronary Events After Myocardial Infarction in Patients With Average Cholesterol Levels," Circulation, Journal of the American Heart Association, 98, pp. 839-844 (1998).
Roger, et al., "Heart Disease and Stroke Statistics—2011 Update: A Report from the American Heart Association," Circulation, Journal of the American Heart Association. Available at http://circ.ahajournals.org/content/123/4/e18 (2010).
Romanovsky, et al., "The vagus nerve in the thermoregulatory response to systemic inflammation," Am. J. Physiol., 273, pp. R407-R413 (1997).
Rossi, et al., "Epicardial ganglionated plexus stimulation decreases postoperative inflammatory response in humans," Heart Rhythm, vol. 9, No. 6, pp. 943-950 (Jun. 2012).
Rouse, et al., "The haemodynamic actions of ZENCA ZD7288, a novel sino-atrial node function modulator, in the exercising beagle: a comparison with zategradine and propranolol," Abstract, British Journal of Pharmacology, 113(3):1071-7 (1994).
Rozman, et al., "Heart function influenced by selective mid-cervical left vagus nerve stimulation in a human case study," Hypertension Research, 32, pp. 1041-1043 (2009).
Rutecki, "Anatomical, Physiological and Theoretical Basis for the Antiepileptic Effect of Vagus Nerve Stimulation," Epilepsia, 31 (suppl. 2), pp. S1-S6 (1990).
Sabbah et al., "Vagus Nerve Stimulation in Experimental Heart Failure," Heart Failure Reviews, vol. 16, No. 2, Mar. 2011, pp. 171-178.
Sabbah, et al., "3722: Vagus nerve stimulation improves left ventricular function in heart failure: results of a 6 month investigation with a cross-over design in dogs with experimental heart failure," European Heart Journal, 32 (Abstract Supplement), pp. 642 (2011).
Sabbah, et al., "Baroreflex Activation Therapy for the Treatment of Heart Failure," Presentation available at http://www.cvrx.com/wp/wp-contenUuploads/2012/04/Dr.-Sabbah-Slides.pdf (2012).
Sabbah, et al., "Chronic Electrical Stimulation of the Carotid Sinus Baroreflex Improves Left Ventricular Function and Promotes Reversal of Ventricular Remodeling in Dogs with Advanced Heart Failure," Circulation Heart Failure, Journal of the American Heart Association, 4, pp. 65-70 (2011).

(56) References Cited

OTHER PUBLICATIONS

Samara, et al., "The Effects of Cardiac Resynchronization Therapy on Chronotropic Incompetence in Patients Intolerant of Beta Antagonist Therapy," Journal of Cardiac Failure, vol. 17, No. 8S, pp. S54-S55 (Aug. 2011).
Sanner, et al., "P4743: Prediction of cardiovascular risk from nocturnal pulse wave signal using the autonomic state indicator (ASI) technology," European Heart Journal, 32 (Abstract Supplement), pp. 839 (2011).
Sato, et al., "Serial Circulating Concentrations of C-Reactive Protein, Interleukin (IL)-4, and IL-6 in Patients with Acute Left Heart Decompensation," Clin. Cardiol. 22, pp. 811-813 (1999).
Schauerte, "Time for Change: Cardiac neurophysiology meets cardiac electrophysiology," Editorial Commentary, Heart Rhythm Society (2013).
Schiereck, et al., "AV blocking due to asynchronous vagal stimulation in rats," Am J Physiol Heart Gire Physiol, 278, pp. H67-H73 (2000).
Schocken, et al., "Prevalence and Mortality Rate of Congestive Heart Failure in the United States," JACC, vol. 20, No. 2, pp. 301-306 (Aug. 1992).
Schwartz, "Vagal Stimulation for Heart Diseases: From Animals to Men," Circulation Journal, vol. 75, pp. 20-27 (Jan. 2011).
Schwartz, "Vagal stimulation for heart failure," Current Opinion in Cardiology, 26, pp. 51-54 (2011).
Schwartz, "Vagal stimulation for the treatment of heart failure: a translational success story," Heart, vol. 98, No. 23, pp. 1687-1690 (2012).
Schwartz, et al. Vagal stimulation for heart failure: Background and first in-man study, Heart Rhythm, 6, 11 suppl., pp. S76-S81 (Nov. 2009).
Schwartz, et al., "Autonomic mechanisms and sudden death. New insights from analysis of baroreceptor reflexes in conscious dogs with and without myocardial infarction," Circulation, Journal of the American Heart Association, 78, pp. 969-979 (1988).
Schwartz, et al., "Effects of Unilateral Cardiac Sympathetic Denervation on the Ventricular Fibrillation Threshold," The American Journal of Cardiology, vol. 37, pp. 1034-1040 (Jun. 1976).
Schwartz, et al., "Long term vagal stimulation in patients with advanced heart failure. First experience in man," European Journal of Heart Failure, 10, pp. 884-891 (2008).
Schwartz, et al., "Sympathetic-parasympathetic interaction in health and disease: abnormalities and relevance in heart failure," Heart Fail Rev, 16, pp. 101-107 (2011).
Seta, et al., "Basic Mechanisms in Heart Failure: The Cytokine Hypothesis," Journal of Cardiac Failure, vol. 2, No. 3, pp. 243-249 (1996).
Sha, et al., "Low-Level Right Vagal Stimulation: Anticholinergic and Antiadrenergic Effects," J Cardiovasc Electrophysiol, pp. 1-7 (Feb. 2011).
Shamoon, et al., The Diabetes Control and Complications Trial Research Group, "The effect of intensive treatment of diabetes on the development and progression of long-term complications in insulin-dependent diabetes mellitus," The New England Journal of Medicine, vol. 329, No. 14, pp. 977-986 (Sep. 30, 1993).
Shannon, "A Model of Safe Levels for Electrical Stimulation," IEEE Transactions on Biomedical Engineering, vol. 39, No. 4, pp. 424-426 (Apr. 1992).
Shen, et al., "Continuous Low-Level Vagus Nerve Stimulation Reduces Stellate Ganglion Nerve Activity and Paroxysmal Atrial Tachyarrhythmias in Ambulatory Canines," Circulation, Journal of the American Heart Association, 123, pp. 2204-2212 (2011).
Shen, et al., "Low-level vagus nerve stimulation upregulates small conductance calcium-activated potassium channels in the stellate ganglion," Heart Rhythm, vol. 10, No. 6, pp. 910-915 (2013).
Shinohara, et al., "Heart Failure Decreases Nerve Activity in the Right Atrial Ganglionated Plexus," J Cardiovasc Electrophysiol, pp. 1-9 (2011).
Shioi, et al., "Increased Expression of Interleukin-1B and Monocyte Chemotactic and Activating Factor/Monocyte Chemoattractant Protein-1 in the Hypertrophied and Failing Heart with Pressure Overload," Gire Res., 81, pp. 664-671 (1997).
Singal, et al., "The role of oxidative stress in the genesis of heart disease," Cardiovascular Research, 40, pp. 426-432 (1998).
Spuck, et al., "Right-sided vagus nerve stimulation in humans: An effective therapy?" Epilepsy Research, pp. 1-3 (2008).
Stein, et al., "A Simple Method to Identify Sleep Apnea Using Holter Recordings," J Cardiovasc Electrophysiol, vol. 14, pp. 467-473 (May 2003).
Stein, et al., "Feasibility of Using Mobile Cardiac Outpatient Telemetry (MCOT) to Identify Severe Sleep Disorders" (2009).
Stieber, et al., "Bradycardic and proarrhythmic properties of sinus node inhibitors," Abstract, Molecular Pharmacology, 69(4):1328-37 (2006).
Taylor, et al., "The unequal influences of the left and right vagi on the control of the heart and pulmonary artery in the rattlesnake, *Grata/us durissus*," The Journal of Experimental Biology, 212, pp. 145-151 (2009).
Thayer, et al., "The role of vagal function in the risk for cardiovascular disease and mortality," Biological Psychology, 74, pp. 224-242 (2007).
Thollon, et al., "Electrophysiological effects of S 16257, a novel sino-atrial node modulator, on rabbit and guinea-pig cardiac preparations: comparison with UL-FS 49," Abstract, British Journal of Pharmacology, 112(1):37-42 (1994).
Tosato, et al., "Quasi-trapezoidal pulses to selectively block the activation of intrinsic laryngeal muscles during vagal nerve stimulation," J. Neural Eng., 4, pp. 205-212 (2007).
Tsutsumi, et al., "Modulation of the myocardial redox state by vagal nerve stimulation after experimental myocardial infarction," Cardiovascular Research, 77, pp. 713-721 (2008).
Tyler, et al., "Chapter 17—Electrodes for the Neural Interface," Neuromodulation, Academic Press (2009).
Ulphani, et al., "Quantitative analysis of parasympathetic innervation of the porcine heart," Heart Rhythm, 7, pp. 1113-1119 (2010).
Uthman, et al., "Effectiveness of vagus nerve stimulation in epilepsy patients. A 12-year observation," Neurology, 63, pp. 1124-1126 (2004).
Van Stee, "Autonomic Innervation of the Heart," Environmental Health Perspectives, vol. 26, pp. 151-158 (1978).
Vanoli, et al., "Vagal stimulation and prevention of sudden death in conscious dogs with a healed myocardial infarction," Circulation Research, Journal of the American Heart Association, 68, pp. 1471-1481 (1991).
Vasan, et al., "Inflammatory Markers and Risk of Heart Failure in Elderly Subjects Without Prior Myocardial Infarction," Circulation, Journal of the American Heart Association, 107, pp. 1486-1491 (2003).
Vassalle, et al., "An Analysis of Arrhythmias Induced by Ouabain in Intact Dogs," Circulation Research, Journal of the American Heart Association, 13, pp. 132-148 (1963).
Velagaleti, et al., "Long-Term Trends in the Incidence of heart Failure After Myocardial Infarction," 118, pp. 2057-2062 (2008).
Verrier, et al., "Microvolt T-Wave Alternans," Journal of the American College of Cardiology, vol. 58, No. 13, pp. 1309-1324 (2011).
Vimercati, et al., "Acute vagal stimulation attenuates cardiac metabolic response to B-adrenergic stress," The Journal of Physiology, vol. 500, No. 23, pp. 6065-6074 (2012).
Wang, et al., "Nicotinic acetylcholine receptor alpha-7 subunit is an essential regulator of inflammation," Nature, vol. 421, pp. 384-388 (Jan. 23, 2003).
Wang, et al., "Synaptic and Neurotransmitter Activation of Cardiac Vagal Neurons in the Nucleus Ambiguus," Annals New York Academy of Sciences, pp. 237-246 (2001).
Waninger, et al., "Characterization of Atrioventricular Nodal Response to Electrical Left Vagal Stimulation," Annals of Biomedical Engineering, vol. 27, pp. 758-762 (1999).
Wann, "Behavioural signs of depression and apoptosis in the limbic system following myocardial infarction: effects of sertraline," Journal of Psychopharmacology, 23(4), pp. 451-459 (2009).

(56) References Cited

OTHER PUBLICATIONS

Wann, et al., "Vulnerability for apoptosis in the limbic system after myocardial infarction in rats: a possible model for human postinfarct major depression," J Psychiatry Neurosci, 32(1):11-6, pp. 11-16 (2007).
Watkins, et al., "Cytokine-to-Brain Communication: A Review & Analysis of Alternative Mechanisms," Life Sciences, vol. 57, No. 11, pp. 1011-1026 (1995).
Whyte, et al., "Reactive oxygen species modulate neuronal excitability in rat intrinsic cardiac ganglia," Auton Neurosci, 150(1-2), pp. 45-52 (Oct. 5, 2009).
Yang, et al., "Sustained increases in heart rate induced by time repetition of vagal stimulation in dogs," Am. J. Physiol., 249, pp. H703-H709 (1985).
Yin, et al., "Independent prognostic value of elevated high-sensitivity C-reactive protein in chronic heart failure," American Heart Journal, vol. 147, No. 5, pp. 931-938 (2004).
Yndestad, et al., "Systemic inflammation in heart failure—The whys and wherefores," Heart Fail Rev, 11, pp. 83-92 (2006).
Yoo, et al., "High-resolution measurement of electrically-evoked vagus nerve activity in the anesthetized dog," J. Neural Eng., 10, pp. 1-9 (2013).
Yoo, et al., "Selective Control of Physiological Responses by Temporally-Patterned Electrical Stimulation of the Canine Vagus Nerve," 33rd Annual International Conference of the IEEE EMBS (2011).
Yu, et al., "Interactions between atrial electrical remodeling and autonomic remodeling: How to break the vicious cycle," Heart Rhythm, 9, pp. 804-809 (2012).
Yu, et al., "Low-level transcutaneous electrical stimulation of the auricular branch of the vagus nerve: A noninvasive approach to treat the initial phase of atrial fibrillation," Heart Rhythm, 10, pp. 428-435 (2013).
Yuan, et al., "Gross and Microscopic Anatomy of the Canine Intrinsic Cardiac Nervous System," The Anatomical Record, 239, pp. 75-87 (1994).
Yusuf, et al., "Changes in Hypertension Treatment and in Congestive Heart Failure Mortality in the United States," Hypertension, Journal of the American Heart Association, 13:174-1179 (1989).
Zhang, et al., "Arrhythmias and vagus nerve stimulation," Heart Fail Rev, 16, pp. 147-161 (2011).
Zhang, et al., "Involvement of activated astrocyte and microglia of locus coeruleus in cardiac pain processing after acute cardiac injury," Neurol Res, 31, pp. 432-438 (2009).
Zhang, et al., "Relationship between right cervical vagus nerve stimulation and atrial fibrillation inducibility: Therapeutic intensities do not increase arrhythmogenesis," Heart Rhythm, 6, pp. 244-250 (2009).
Zhang, et al., "Therapeutic Effects of Selective Atrioventricular Node Vagal Stimulation in Atrial Fibrillation and Heart Failure," Journal of Cardiovascular Electrophysiology, vol. 24, Issue 1, pp. 86-91 (2012).
Zheng, et al., "Vagal stimulation markedly suppresses arrhythmias in conscious rats with chronic heart failure after myocardial infarction," Proceedings of the 2005 IEEE (2005).
Zipes, et al., "Effects of selective vagal and stellate ganglion stimulation on atrial refractoriness," Cardiovascular Research, 8, pp. 647-655 (1974).
Zucker, et al., "Chronic Baroreceptor Activation Enhances Survival in Dogs with Pacing-Induced Heart Failure," Journal of the American Heart Association, Hypertension (2007).

\* cited by examiner

RESPONSIVE NEUROSTIMULATION FOR THE TREATMENT OF CHRONIC CARDIAC DYSFUNCTION

CROSS-REFERENCE TO RELATED APPLICATIONS

This application is a Continuation of U.S. patent application Ser. No. 14/861,390, now U.S. Pat. No. 9,446,237, filed Sep. 22, 2015, which claims the benefit of and priority to U.S. application Ser. No. 14/271,714, now U.S. Pat. No. 9,272,143, filed May 7, 2014, both of which are hereby incorporated herein by reference in their entireties.

FIELD

This application relates to neuromodulation.

BACKGROUND

Chronic heart failure (CHF) and other forms of chronic cardiac dysfunction (CCD) may be related to an autonomic imbalance of the sympathetic and parasympathetic nervous systems that, if left untreated, can lead to cardiac arrhythmogenesis, progressively worsening cardiac function, and eventual patient death. CHF is pathologically characterized by an elevated neuroexcitatory state and is accompanied by physiological indications of impaired arterial and cardiopulmonary baroreflex function with reduced vagal activity.

CHF triggers compensatory activations of the sympathoadrenal (sympathetic) nervous system and the renin-angiotensin-aldosterone hormonal system, which initially helps to compensate for deteriorating heart-pumping function, yet, over time, can promote progressive left ventricular dysfunction and deleterious cardiac remodeling. Patients suffering from CHF are at increased risk of tachyarrhythmias, such as atrial fibrillation (AF), ventricular tachyarrhythmias (ventricular tachycardia (VT) and ventricular fibrillation (VF)), and atrial flutter, particularly when the underlying morbidity is a form of coronary artery disease, cardiomyopathy, mitral valve prolapse, or other valvular heart disease. Sympathoadrenal activation also significantly increases the risk and severity of tachyarrhythmias due to neuronal action of the sympathetic nerve fibers in, on, or around the heart and through the release of epinephrine (adrenaline), which can exacerbate an already-elevated heart rate.

The standard of care for managing CCD in general continues to evolve. For instance, new therapeutic approaches that employ electrical stimulation of neural structures that directly address the underlying cardiac autonomic nervous system imbalance and dysregulation have been proposed. In one form, controlled stimulation of the cervical vagus nerve beneficially modulates cardiovascular regulatory function. Vagus nerve stimulation (VNS) has been used for the clinical treatment of drug-refractory epilepsy and depression, and more recently has been proposed as a therapeutic treatment of heart conditions such as CHF. For instance, VNS has been demonstrated in canine studies as efficacious in simulated treatment of AF and heart failure, such as described in Zhang et al., "Chronic Vagus Nerve Stimulation Improves Autonomic Control and Attenuates Systemic Inflammation and Heart Failure Progression in a Canine High-Rate Pacing Model," Circ Heart Fail 2009, 2, pp. 692-699 (Sep. 22, 2009), the disclosure of which is incorporated by reference. The results of a multi-center open-label phase II study in which chronic VNS was utilized for CHF patients with severe systolic dysfunction is described in De Ferrari et al., "Chronic Vagus Nerve Stimulation: A New and Promising Therapeutic Approach for Chronic Heart Failure," European Heart Journal, 32, pp. 847-855 (Oct. 28, 2010).

VNS therapy commonly requires implantation of a neurostimulator, a surgical procedure requiring several weeks of recovery before the neurostimulator can be activated and a patient can start receiving VNS therapy. Even after the recovery and activation of the neurostimulator, a full therapeutic dose of VNS is not immediately delivered to the patient to avoid causing significant patient discomfort and other undesirable side effects. Instead, to allow the patient to adjust to the VNS therapy, a titration process is utilized in which the intensity is gradually increased over a period of time under the control of a physician, with the patient given time between successive increases in VNS therapy intensity to adapt to the new intensity. As stimulation is chronically applied at each new intensity level, the patient's side effect threshold gradually increases, allowing for an increase in intensity during subsequent titration sessions.

Conventional general therapeutic alteration of cardiac vagal efferent activation through electrical stimulation targets only the efferent nerves of the parasympathetic nervous system, such as described in Sabbah et al., "Vagus Nerve Stimulation in Experimental Heart Failure," Heart Fail. Rev., 16:171-178 (2011), the disclosure of which is incorporated by reference. The Sabbah paper discusses canine studies using a vagus nerve stimulation system, manufactured by BioControl Medical Ltd., Yehud, Israel, which includes an electrical pulse generator, right ventricular endocardial sensing lead, and right vagus nerve cuff stimulation lead. The sensing lead enables stimulation of the right vagus nerve in a highly specific manner, which includes closed-loop synchronization of the vagus nerve stimulation pulse to the cardiac cycle. An asymmetric tri-polar nerve cuff electrode is implanted on the right vagus nerve at the mid-cervical position. The electrode provides cathodic induction of action potentials while simultaneously applying asymmetric anodal block that leads to preferential activation of vagal efferent fibers. Electrical stimulation of the right cervical vagus nerve is delivered only when heart rate is above a preset threshold. Stimulation is provided at an intensity intended to reduce basal heart rate by ten percent by preferential stimulation of efferent vagus nerve fibers leading to the heart while blocking afferent neural impulses to the brain. Although effective in partially restoring baroreflex sensitivity, increasing left ventricular ejection fraction, and decreasing left ventricular end diastolic and end systolic volumes, a portion of the therapeutic benefit is due to incidental recruitment of afferent parasympathetic nerve fibers in the vagus. Efferent stimulation alone is less effective than bidirectional stimulation at restoring autonomic balance.

Accordingly, a need remains for an approach to efficiently providing neurostimulation therapy, and, in particular, to neurostimulation therapy for treating chronic cardiac dysfunction and other conditions.

SUMMARY

In accordance with embodiments of the present invention, a neurostimulation system is provided, comprising: an electrode assembly; a neurostimulator coupled to the electrode assembly, said neurostimulator adapted to deliver a stimulation signal to a patient in the patient's neural fulcrum zone, said stimulation signal comprising an ON time and an OFF time; a physiological sensor configured to acquire a physiological signal from the patient; and a control system coupled to the neurostimulator and the physiological sensor. The control system is programmed to: monitor a baseline signal acquired by the physiological sensor during the OFF time periods of the stimulation signal; monitor a response signal acquired by the physiological sensor during the ON time periods of the stimulation signal; and in response to the monitored baseline signal and the monitored response signal, adjust one or more parameters of the stimulation signal to deliver the stimulation signal in the patient's neural fulcrum zone.

In accordance with other embodiments of the present, a method of operating an implantable medical device (IMD) comprising a physiological sensor configured to acquire a physiological signal from the patient, and a neurostimulator coupled to an electrode assembly, said neurostimulator adapted to deliver a stimulation signal to a patient. The method comprises: activating the neurostimulator to deliver a stimulation signal in a patient's neural fulcrum zone, said stimulation signal comprising an ON time and an OFF time; monitoring a baseline signal acquired by the physiological sensor during the OFF time periods of the stimulation signal; monitoring a response signal acquired by the physiological sensor during the ON time periods of the stimulation signal; and in response to the monitored baseline signal and the monitored response signal, adjusting one or more parameters of the stimulation signal to deliver the stimulation signal in the patient's neural fulcrum zone.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

CHF and other cardiovascular diseases cause derangement of autonomic control of the cardiovascular system, favoring increased sympathetic and decreased parasympathetic central outflow. These changes are accompanied by elevation of basal heart rate arising from chronic sympathetic hyperactivation along the neurocardiac axis.

The vagus nerve is a diverse nerve trunk that contains both sympathetic and parasympathetic fibers, and both afferent and efferent fibers. These fibers have different diameters and myelination, and subsequently have different activation thresholds. This results in a graded response as intensity is increased. Low intensity stimulation results in a progressively greater tachycardia, which then diminishes and is replaced with a progressively greater bradycardia response as intensity is further increased. Peripheral neurostimulation therapies that target the fluctuations of the autonomic nervous system have been shown to improve clinical outcomes in some patients. Specifically, autonomic regulation therapy results in simultaneous creation and propagation of efferent and afferent action potentials within nerve fibers comprising the cervical vagus nerve. The therapy directly improves autonomic balance by engaging both medullary and cardiovascular reflex control components of the autonomic nervous system. Upon stimulation of the cervical vagus nerve, action potentials propagate away from the stimulation site in two directions: efferently toward the heart and afferently toward the brain. Efferent action potentials influence the intrinsic cardiac nervous system and the heart and other organ systems, while afferent action potentials influence central elements of the nervous system.

Figure 1:
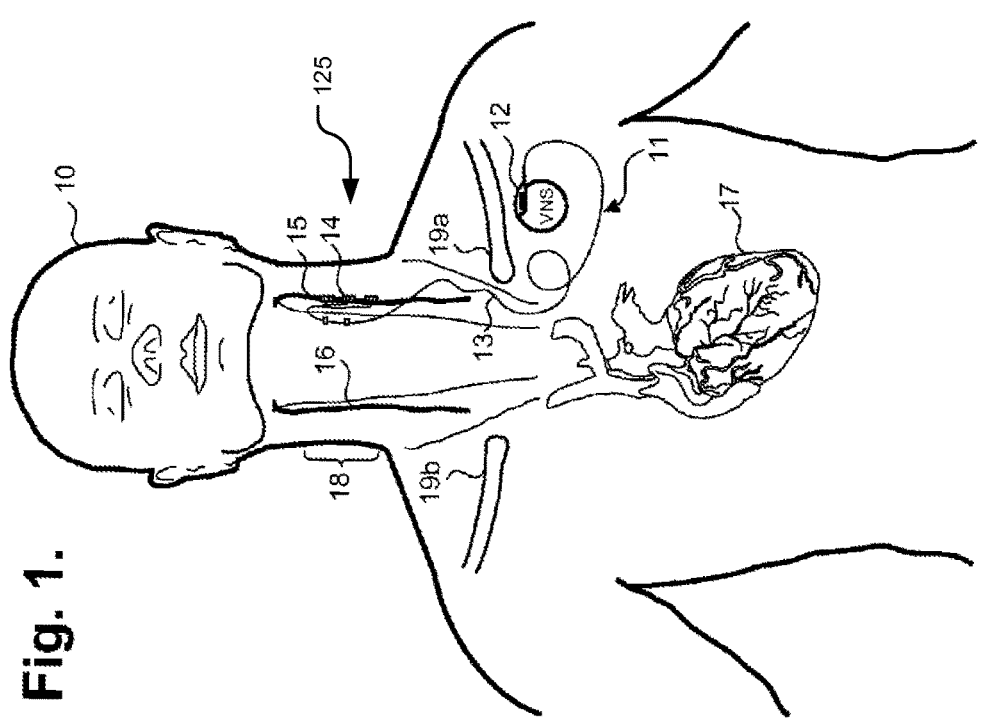
FIG. 1 is a front anatomical diagram showing, by way of example, placement of an implantable vagus stimulation device in a male patient, in accordance with one embodiment.

An implantable vagus nerve stimulator, such as used to treat drug-refractory epilepsy and depression, can be adapted for use in managing chronic cardiac dysfunction (CCD) through therapeutic bi-directional vagus nerve stimulation. FIG. 1 is a front anatomical diagram showing, by way of example, placement of an implantable medical device (e.g., a vagus nerve stimulation (VNS) system 11, as shown in FIG. 1) in a male patient 10, in accordance with embodiments of the present invention. The VNS provided through the stimulation system 11 operates under several mechanisms of action. These mechanisms include increasing parasympathetic outflow and inhibiting sympathetic effects by inhibiting norepinephrine release and adrenergic receptor activation. More importantly, VNS triggers the release of the endogenous neurotransmitter acetylcholine and other peptidergic substances into the synaptic cleft, which has several beneficial anti-arrhythmic, anti-apoptotic, and anti-inflammatory effects as well as beneficial effects at the level of the central nervous system.

The implantable vagus stimulation system 11 comprises an implantable neurostimulator or pulse generator 12 and a stimulating nerve electrode assembly 125. The stimulating nerve electrode assembly 125, preferably comprising at least an electrode pair, is conductively connected to the distal end of an insulated, electrically conductive lead assembly 13 and electrodes 14. The electrodes 14 may be provided in a variety of forms, such as, e.g., helical electrodes, probe electrodes, cuff electrodes, as well as other types of electrodes. The implantable vagus stimulation system 11 can be remotely accessed following implant through an external programmer, such as the programmer 40 shown in FIG. 3 and described in further detail below. The programmer 40 can be used by healthcare professionals to check and program the neurostimulator 12 after implantation in the patient 10. In some embodiments, an external magnet may provide basic controls, such as described in commonly assigned U.S. Pat. No. 8,600,505, entitled "Implantable Device For Facilitating Control Of Electrical Stimulation Of Cervical Vagus Nerves For Treatment Of Chronic Cardiac Dysfunction," the disclosure of which is incorporated by reference. For further example, an electromagnetic controller may enable the patient 10 or healthcare professional to interact with the implanted neurostimulator 12 to exercise increased control over therapy delivery and suspension, such as described in commonly assigned U.S. Pat. No. 8,571,654, entitled "Vagus Nerve Neurostimulator With Multiple Patient-Selectable Modes For Treating Chronic Cardiac Dysfunction," the disclosure of which is incorporated by reference. For further example, an external programmer may communicate with the neurostimulation system 11 via other wired or wireless communication methods, such as, e.g., wireless RF transmission. Together, the implantable vagus stimulation system 11 and one or more of the external components form a VNS therapeutic delivery system.

The neurostimulator 12 is typically implanted in the patient's right or left pectoral region generally on the same side (ipsilateral) as the vagus nerve 15, 16 to be stimulated, although other neurostimulator-vagus nerve configurations, including contra-lateral and bi-lateral are possible. A vagus nerve typically comprises two branches that extend from the brain stem respectively down the left side and right side of the patient, as seen in FIG. 1. The electrodes 14 are generally implanted on the vagus nerve 15, 16 about halfway between the clavicle 19a-b and the mastoid process. The electrodes may be implanted on either the left or right side. The lead assembly 13 and electrodes 14 are implanted by first exposing the carotid sheath and chosen branch of the vagus nerve 15, 16 through a latero-cervical incision (perpendicular to the long axis of the spine) on the ipsilateral side of the patient's neck 18. The helical electrodes 14 are then placed onto the exposed nerve sheath and tethered. A subcutaneous tunnel is formed between the respective implantation sites of the neurostimulator 12 and helical electrodes 14, through which the lead assembly 13 is guided to the neurostimulator 12 and securely connected.

In one embodiment, the neural stimulation is provided as a low-level maintenance dose independent of cardiac cycle. The stimulation system 11 bi-directionally stimulates either the left vagus nerve 15 or the right vagus nerve 16. However, it is contemplated that multiple electrodes 14 and multiple leads 13 could be utilized to stimulate simultaneously, alternatively, or in other various combinations. Stimulation may be through multimodal application of continuously cycling, intermittent and periodic electrical stimuli, which are parametrically defined through stored stimulation parameters and timing cycles. Both sympathetic and parasympathetic nerve fibers in the vagosympathetic complex are stimulated. A study of the relationship between cardiac autonomic nerve activity and blood pressure changes in ambulatory dogs is described in J. Hellyer et al., "Autonomic Nerve Activity and Blood Pressure in Ambulatory Dogs," Heart Rhythm, Vol. 11(2), pp. 307-313 (February 2014). Generally, cervical vagus nerve stimulation results in propagation of action potentials from the site of stimulation in a bi-directional manner. The application of bi-directional propagation in both afferent and efferent directions of action potentials within neuronal fibers comprising the cervical vagus nerve improves cardiac autonomic balance. Afferent action potentials propagate toward the parasympathetic nervous system's origin in the medulla in the nucleus ambiguus, nucleus tractus solitarius, and the dorsal motor nucleus, as well as toward the sympathetic nervous system's origin in the intermediolateral cell column of the spinal cord. Efferent action potentials propagate toward the heart 17 to activate the components of the heart's intrinsic nervous system. Either the left or right vagus nerve 15, 16 can be stimulated by the stimulation system 11. The right vagus nerve 16 has a moderately lower (approximately 30%) stimulation threshold than the left vagus nerve 15 for heart rate effects at the same stimulation frequency and pulse width.

Figure 2A:
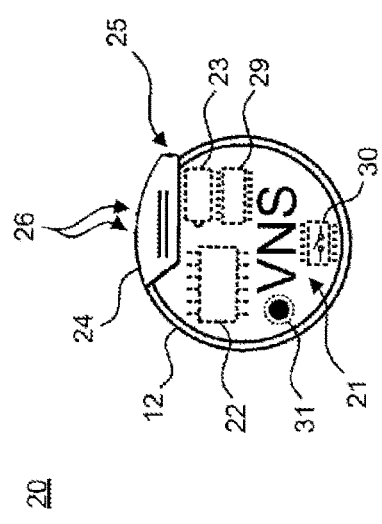
FIGS. 2A and 2B are diagrams respectively showing the implantable neurostimulator and the simulation therapy lead of FIG. 1.
Figure 2B:
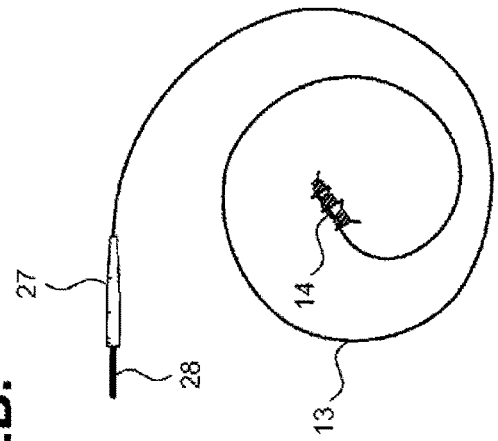

The VNS therapy is delivered autonomously to the patient's vagus nerve 15, 16 through three implanted components that include a neurostimulator 12, lead assembly 13, and electrodes 14. FIGS. 2A and 2B are diagrams respectively showing the implantable neurostimulator 12 and the stimulation lead assembly 13 of FIG. 1. In one embodiment, the neurostimulator 12 can be adapted from a VNS Therapy Demipulse Model 103 or AspireSR Model 106 pulse generator, manufactured and sold by Cyberonics, Inc., Houston, Tex., although other manufactures and types of implantable VNS neurostimulators could also be used. The stimulation lead assembly 13 and electrodes 14 are generally fabricated as a combined assembly and can be adapted from a Model 302 lead, PerenniaDURA Model 303 lead, or PerenniaFLEX Model 304 lead, also manufactured and sold by Cyberonics, Inc., in two sizes based, for example, on a helical electrode inner diameter, although other manufactures and types of single-pin receptacle-compatible therapy leads and electrodes could also be used.

Referring first to FIG. 2A, the system 20 may be configured to provide multimodal vagus nerve stimulation. In a maintenance mode, the neurostimulator 12 is parametrically programmed to deliver continuously cycling, intermittent and periodic ON-OFF cycles of VNS. Such delivery produces action potentials in the underlying nerves that propagate bi-directionally, both afferently and efferently.

The neurostimulator 12 includes an electrical pulse generator that is tuned to improve autonomic regulatory function by triggering action potentials that propagate both afferently and efferently within the vagus nerve 15, 16. The neurostimulator 12 is enclosed in a hermetically sealed housing 21 constructed of a biocompatible material, such as titanium. The housing 21 contains electronic circuitry 22 powered by a battery 23, such as a lithium carbon monofluoride primary battery or a rechargeable secondary cell battery. The electronic circuitry 22 may be implemented using complementary metal oxide semiconductor integrated circuits that include a microprocessor controller that executes a control program according to stored stimulation parameters and timing cycles; a voltage regulator that regulates system power; logic and control circuitry, including a recordable memory 29 within which the stimulation parameters are stored, that controls overall pulse generator function, receives and implements programming commands from the external programmer, or other external source, collects and stores telemetry information, processes sensory input, and controls scheduled and sensory-based therapy outputs; a transceiver that remotely communicates with the external programmer using radio frequency signals; an antenna, which receives programming instructions and transmits the telemetry information to the external programmer; and a reed switch 30 that provides remote access to the operation of the neurostimulator 12 using an external programmer, a simple patient magnet, or an electromagnetic controller. The recordable memory 29 can include both volatile (dynamic) and non-volatile/persistent (static) forms of memory, such as firmware within which the stimulation parameters and timing cycles can be stored. Other electronic circuitry and components are possible.

The neurostimulator 12 includes a header 24 to securely receive and connect to the lead assembly 13. In one embodiment, the header 24 encloses a receptacle 25 into which a single pin for the lead assembly 13 can be received, although two or more receptacles could also be provided, along with the corresponding electronic circuitry 22. The header 24 internally includes a lead connector block (not shown) and a set of screws 26.

In some embodiments, the housing 21 may also contain a heart rate sensor 31 that is electrically interfaced with the logic and control circuitry, which receives the patient's sensed heart rate as sensory inputs. The heart rate sensor 31 monitors heart rate using an ECG-type electrode. Through the electrode, the patient's heartbeat can be sensed by detecting ventricular depolarization. In a further embodiment, a plurality of electrodes can be used to sense voltage differentials between electrode pairs, which can undergo signal processing for cardiac physiological measures, for instance, detection of the P-wave, QRS complex, and T-wave. The heart rate sensor 31 provides the sensed heart rate to the control and logic circuitry as sensory inputs that can be used to determine the onset or presence of arrhythmias, particularly VT, and/or to monitor and record changes in the patient's heart rate over time or in response to applied stimulation signals.

Referring next to FIG. 2B, the lead assembly 13 delivers an electrical signal from the neurostimulator 12 to the vagus nerve 15, 16 via the electrodes 14. On a proximal end, the lead assembly 13 has a lead connector 27 that transitions an insulated electrical lead body to a metal connector pin 28. During implantation, the connector pin 28 is guided through the receptacle 25 into the header 24 and securely fastened in place using the setscrews 26 to electrically couple the lead assembly 13 to the neurostimulator 12. On a distal end, the lead assembly 13 terminates with the electrodes 14, which bifurcates into a pair of anodic and cathodic electrodes 62 (as further described infra with reference to FIG. 4). In one embodiment, the lead connector 27 is manufactured using silicone and the connector pin 28 is made of stainless steel, although other suitable materials could be used, as well. The insulated lead body 13 utilizes a silicone-insulated alloy conductor material.

In some embodiments, the electrodes 14 are helical and placed around the cervical vagus nerve 15, 16 at the location below where the superior and inferior cardiac branches separate from the cervical vagus nerve. In alternative embodiments, the helical electrodes may be placed at a location above where one or both of the superior and inferior cardiac branches separate from the cervical vagus nerve. In one embodiment, the helical electrodes 14 are positioned around the patient's vagus nerve oriented with the end of the helical electrodes 14 facing the patient's head. In an alternate embodiment, the helical electrodes 14 are positioned around the patient's vagus nerve 15, 16 oriented with the end of the helical electrodes 14 facing the patient's heart 17. At the distal end, the insulated electrical lead body 13 is bifurcated into a pair of lead bodies that are connected to a pair of electrodes. The polarity of the electrodes could be configured into a monopolar cathode, a proximal anode and a distal cathode, or a proximal cathode and a distal anode.

Figure 3:
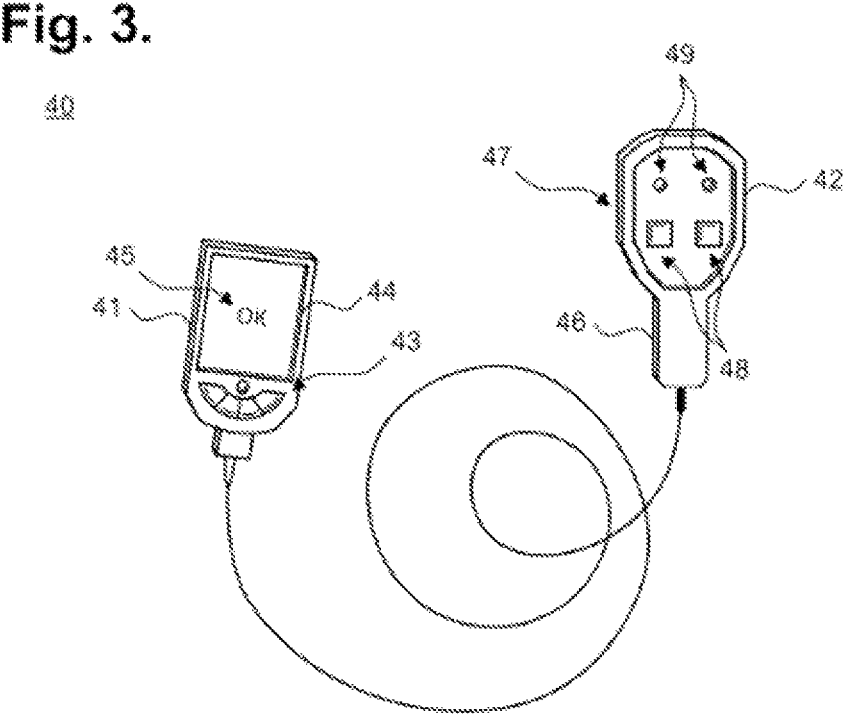
FIG. 3 is a diagram showing an external programmer for use with the implantable neurostimulator of FIG. 1.

The neurostimulator 12 may be interrogated prior to implantation and throughout the therapeutic period with a healthcare provider-operable control system comprising an external programmer and programming wand (shown in FIG. 3) for checking proper operation, downloading recorded data, diagnosing problems, and programming operational parameters, such as described in commonly assigned U.S. Pat. Nos. 8,600,505 and 8,571,654, cited supra. FIG. 3 is a diagram showing an external programmer 40 for use with the implantable neurostimulator 12 of FIG. 1. The external programmer 40 includes a healthcare provider operable programming computer 41 and a programming wand 42. Generally, use of the external programmer is restricted to healthcare providers, while more limited manual control is provided to the patient through "magnet mode."

In one embodiment, the external programmer 40 executes application software 45 specifically designed to interrogate the neurostimulator 12. The programming computer 41 interfaces to the programming wand 42 through a wired or wireless data connection. The programming wand 42 can be adapted from a Model 201 Programming Wand, manufactured and sold by Cyberonics, Inc., and the application software 45 can be adapted from the Model 250 Programming Software suite, licensed by Cyberonics, Inc. Other configurations and combinations of external programmer 40, programming wand 42, and application software 45 are possible.

The programming computer 41 can be implemented using a general purpose programmable computer and can be a personal computer, laptop computer, ultrabook computer, netbook computer, handheld computer, tablet computer, smartphone, or other form of computational device. In one embodiment, the programming computer is a tablet computer that may operate under the iOS operating system from Apple Inc., such as the iPad from Apple Inc., or may operate under the Android operating system from Google Inc., such as the Galaxy Tab from Samsung Electronics Co., Ltd. In an alternative embodiment, the programming computer is a personal digital assistant handheld computer operating under the Pocket-PC, Windows Mobile, Windows Phone, Windows RT, or Windows operating systems, licensed by Microsoft Corporation, Redmond, Wash., such as the Surface from Microsoft Corporation, the Dell Axim XS and X50 personal data assistants, sold by Dell, Inc., Round Top, Tex., the HP Jornada personal data assistant, sold by Hewlett-Packard Company, Palo Alto, Calif. The programming computer 41 functions through those components conventionally found in such devices, including, for instance, a central processing unit, volatile and persistent memory, touch-sensitive display, control buttons, peripheral input and output ports, and network interface. The computer 41 operates under the control of the application software 45, which is executed as program code as a series of process or method modules or steps by the programmed computer hardware. Other assemblages or configurations of computer hardware, firmware, and software are possible.

Operationally, the programming computer 41, when connected to a neurostimulator 12 through wireless telemetry using the programming wand 42, can be used by a healthcare provider to remotely interrogate the neurostimulator 12 and modify stored stimulation parameters. The programming wand 42 provides data conversion between the digital data accepted by and output from the programming computer and the radio frequency signal format that is required for communication with the neurostimulator 12. The programming computer 41 may further be configured to receive inputs, such as physiological signals received from patient sensors (e.g., implanted or external). These sensors may be configured to monitor one or more physiological signals, e.g., vital signs, such as body temperature, pulse rate, respiration rate, blood pressure, etc. These sensors may be coupled directly to the programming computer 41 or may be coupled to another instrument or computing device that receives the sensor input and transmits the input to the programming computer 41. The programming computer 41 may monitor, record, and/or respond to the physiological signals in order to effectuate stimulation delivery in accordance with embodiments of the present invention.

The healthcare provider operates the programming computer 41 through a user interface that includes a set of input controls 43 and a visual display 44, which could be touch-sensitive, upon which to monitor progress, view downloaded telemetry and recorded physiology, and review and modify programmable stimulation parameters. The telemetry can include reports on device history that provide patient identifier, implant date, model number, serial number, magnet activations, total ON time, total operating time, manufacturing date, and device settings and stimulation statistics, and reports on device diagnostics that include patient identifier, model identifier, serial number, firmware build number, implant date, communication status, output current status, measured current delivered, lead impedance, and battery status. Other kinds of telemetry or telemetry reports are possible.

During interrogation, the programming wand 42 is held by its handle 46, and the bottom surface 47 of the programming wand 42 is placed on the patient's chest over the location of the implanted neurostimulator 12. A set of indicator lights 49 can assist with proper positioning of the wand, and a set of input controls 48 enables the programming wand 42 to be operated directly, rather than requiring the healthcare provider to awkwardly coordinate physical wand manipulation with control inputs via the programming computer 41. The sending of programming instructions and receipt of telemetry information occur wirelessly through radio frequency signal interfacing. Other programming computer and programming wand operations are possible.

Figure 4:
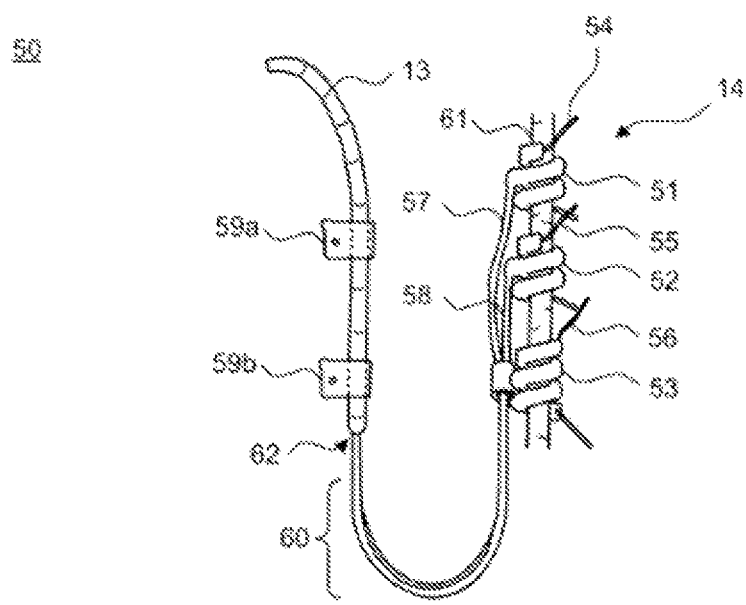
FIG. 4 is a diagram showing electrodes provided as on the stimulation therapy lead of FIG. 2 in place on a vagus nerve in situ.

Preferably, the electrodes 14 are helical and placed on the cervical vagus nerve 15, 16 at the location below where the superior and inferior cardiac branches separate from the cervical vagus nerve. FIG. 4 is a diagram showing the helical electrodes 14 provided as on the stimulation lead assembly 13 of FIG. 2 in place on a vagus nerve 15, 16 in situ 50. Although described with reference to a specific manner and orientation of implantation, the specific surgical approach and implantation site selection particulars may vary, depending upon physician discretion and patient physical structure.

Under one embodiment, helical electrodes 14 may be positioned on the patient's vagus nerve 61 oriented with the end of the helical electrodes 14 facing the patient's head. At the distal end, the insulated electrical lead body 13 is bifurcated into a pair of lead bodies 57, 58 that are connected to a pair of electrodes 51, 52. The polarity of the electrodes 51, 52 could be configured into a monopolar cathode, a proximal anode and a distal cathode, or a proximal cathode and a distal anode. In addition, an anchor tether 53 is fastened over the lead bodies 57, 58 that maintains the position of the helical electrodes on the vagus nerve 61 following implant. In one embodiment, the conductors of the electrodes 51, 52 are manufactured using a platinum and iridium alloy, while the helical materials of the electrodes 51, 52 and the anchor tether 53 are a silicone elastomer.

During surgery, the electrodes 51, 52 and the anchor tether 53 are coiled around the vagus nerve 61 proximal to the patient's head, each with the assistance of a pair of sutures 54, 55, 56, made of polyester or other suitable material, which help the surgeon to spread apart the respective helices. The lead bodies 57, 58 of the electrodes 51, 52 are oriented distal to the patient's head and aligned parallel to each other and to the vagus nerve 61. A strain relief bend 60 can be formed on the distal end with the insulated electrical lead body 13 aligned, for example, parallel to the helical electrodes 14 and attached to the adjacent fascia by a plurality of tie-downs 59a-b.

The neurostimulator 12 delivers VNS under control of the electronic circuitry 22. The stored stimulation parameters are programmable. Each stimulation parameter can be independently programmed to define the characteristics of the cycles of therapeutic stimulation and inhibition to ensure optimal stimulation for a patient 10. The programmable stimulation parameters include output current, signal frequency, pulse width, signal ON time, signal OFF time, magnet activation (for VNS specifically triggered by "magnet mode"), and reset parameters. Other programmable parameters are possible. In addition, sets or "profiles" of preselected stimulation parameters can be provided to physicians with the external programmer and fine-tuned to a patient's physiological requirements prior to being programmed into the neurostimulator 12, such as described in commonly assigned U.S. Pat. No. 8,630,709, entitled "Computer-Implemented System and Method for Selecting Therapy Profiles of Electrical Stimulation of Cervical Vagus Nerves for Treatment of Chronic Cardiac Dysfunction," Ser. No. 13/314,138, filed on Dec. 7, 2011, the disclosure of which is incorporated by reference.

Therapeutically, the VNS may be delivered as a multi-modal set of therapeutic doses, which are system output behaviors that are pre-specified within the neurostimulator 12 through the stored stimulation parameters and timing cycles implemented in firmware and executed by the microprocessor controller. The therapeutic doses include a maintenance dose that includes continuously cycling, intermittent, and periodic cycles of electrical stimulation during periods in which the pulse amplitude is greater than 0 mA ("therapy ON") and during periods in which the pulse amplitude is 0 mA ("therapy OFF").

The neurostimulator 12 can operate either with or without an integrated heart rate sensor, such as respectively described in commonly assigned U.S. Pat. No. 8,577,458, entitled "Implantable Device for Providing Electrical Stimulation of Cervical Vagus Nerves for Treatment of Chronic Cardiac Dysfunction with Leadless Heart Rate Monitoring," and U.S. Patent application, entitled "Implantable Device for Providing Electrical Stimulation of Cervical Vagus Nerves for Treatment of Chronic Cardiac Dysfunction," Ser. No. 13/314,119, filed on Dec. 7, 2011, pending, the disclosures of which are hereby incorporated by reference herein in their entirety. Additionally, where an integrated leadless heart rate monitor is available, the neurostimulator 12 can provide autonomic cardiovascular drive evaluation and self-controlled titration, such as respectively described in commonly-assigned U.S. Pat. No. 8,918,190, entitled "Implantable Device for Evaluating Autonomic Cardiovascular Drive in a Patient Suffering from Chronic Cardiac Dysfunction," Ser. No. 13/314,133, filed on Dec. 7, 2011, and U.S. Pat. No. 8,918,191, entitled "Implantable Device for Providing Electrical Stimulation of Cervical Vagus Nerves for Treatment of Chronic Cardiac Dysfunction with Bounded Titration," Ser. No. 13/314,135, filed on Dec. 7, 2011, the disclosures of which are incorporated by reference. Finally, the neurostimulator 12 can be used to counter natural circadian sympathetic surge upon awakening and manage the risk of cardiac arrhythmias during or attendant to sleep, particularly sleep apneic episodes, such as respectively described in commonly assigned U.S. Pat. No. 8,923,964, entitled "Implantable Neurostimulator-Implemented Method For Enhancing Heart Failure Patient Awakening Through Vagus Nerve Stimulation," Ser. No. 13/673,811, filed on Nov. 9, 2012, the disclosure of which is incorporated by reference.

The VNS stimulation signal may be delivered as a therapy in a maintenance dose having an intensity that is insufficient to elicit undesirable side effects, such as cardiac arrhythmias. The VNS can be delivered with a periodic duty cycle in the range of 2% to 89% with a preferred range of around 4% to 36% that is delivered as a low intensity maintenance dose. Alternatively, the low intensity maintenance dose may comprise a narrow range approximately at 17.5%, such as around 15% to 20%. The selection of duty cycle is a trade-off among competing medical considerations. The duty cycle is determined by dividing the stimulation ON time by the sum of the ON and OFF times of the neurostimulator 12 during a single ON-OFF cycle. However, the stimulation time may also need to include ramp-up time and ramp-down time, where the stimulation frequency exceeds a minimum threshold (as further described infra with reference to FIG. 7).

Figure 5:
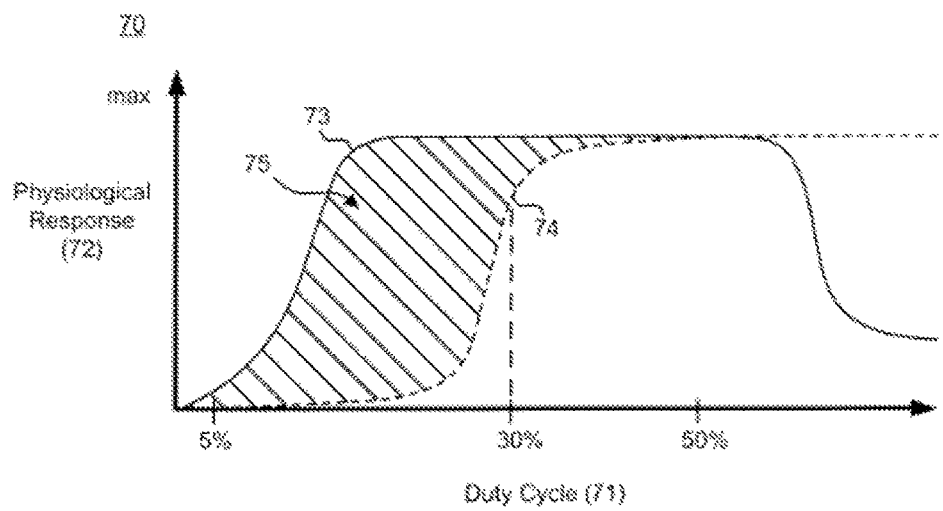
FIG. 5 is a graph showing, by way of example, the relationship between the targeted therapeutic efficacy and the extent of potential side effects resulting from use of the implantable neurostimulator of FIG. 1.

FIG. 5 is a graph 70 showing, by way of example, the relationship between the targeted therapeutic efficacy 73 and the extent of potential side effects 74 resulting from use of the implantable neurostimulator 12 of FIG. 1, after the patient has completed the titration process. The graph in FIG. 5 provides an illustration of the failure of increased stimulation intensity to provide additional therapeutic benefit, once the stimulation parameters have reached the neural fulcrum zone, as will be described in greater detail below with respect to FIG. 8. As shown in FIG. 5, the x-axis represents the duty cycle 71. The duty cycle is determined by dividing the stimulation ON time by the sum of the ON and OFF times of the neurostimulator 12 during a single ON-OFF cycle. However, the stimulation time may also include ramp-up time and ramp-down time, where the stimulation frequency exceeds a minimum threshold (as further described infra with reference to FIG. 7). The y-axis represents physiological response 72 to VNS therapy. The physiological response 72 can be expressed quantitatively for a given duty cycle 71 as a function of the targeted therapeutic efficacy 73 and the extent of potential side effects 74, as described infra. The maximum level of physiological response 72 ("max") signifies the highest point of targeted therapeutic efficacy 73 or potential side effects 74.

Targeted therapeutic efficacy 73 and the extent of potential side effects 74 can be expressed as functions of duty cycle 71 and physiological response 72. The targeted therapeutic efficacy 73 represents the intended effectiveness of VNS in provoking a beneficial physiological response for a given duty cycle and can be quantified by assigning values to the various acute and chronic factors that contribute to the physiological response 72 of the patient 10 due to the delivery of therapeutic VNS. Acute factors that contribute to the targeted therapeutic efficacy 73 include beneficial changes in heart rate variability and increased coronary flow, reduction in cardiac workload through vasodilation, and improvement in left ventricular relaxation. Chronic factors that contribute to the targeted therapeutic efficacy 73 include improved cardiovascular regulatory function, as well as decreased negative cytokine production, increased baroreflex sensitivity, increased respiratory gas exchange efficiency, favorable gene expression, renin-angiotensin-aldosterone system down-regulation, antiarrhythmic, antiapoptotic, and ectopy-reducing anti-inflammatory effects. These contributing factors can be combined in any manner to express the relative level of targeted therapeutic efficacy 73, including weighting particular effects more heavily than others or applying statistical or numeric functions based directly on or derived from observed physiological changes. Empirically, targeted therapeutic efficacy 73 steeply increases beginning at around a 5% duty cycle and levels off in a plateau near the maximum level of physiological response at around a 30% duty cycle. Thereafter, targeted therapeutic efficacy 73 begins decreasing at around a 50% duty cycle and continues in a plateau near a 25% physiological response through the maximum 100% duty cycle.

Figure 6:
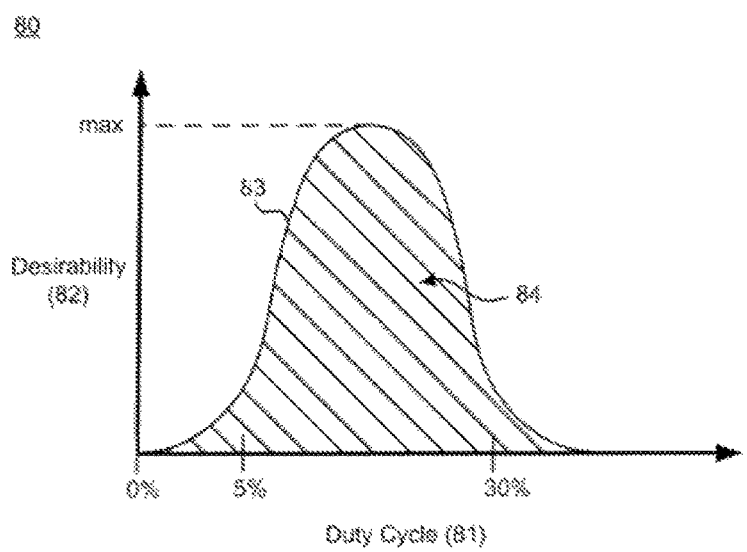
FIG. 6 is a graph showing, by way of example, the optimal duty cycle range based on the intersection depicted in FIG. 3.

The intersection 75 of the targeted therapeutic efficacy 73 and the extent of potential side effects 74 represents one optimal duty cycle range for VNS. FIG. 6 is a graph 80 showing, by way of example, the optimal duty cycle range 83 based on the intersection 75 depicted in FIG. 5. The x-axis represents the duty cycle 81 as a percentage of stimulation time over stimulation time plus inhibition time. The y-axis represents therapeutic points 82 reached in operating the neurostimulator 12 at a given duty cycle 81. The optimal duty range 83 is a function 84 of the intersection 75 of the targeted therapeutic efficacy 73 and the extent of potential side effects 74. The therapeutic operating points 82 can be expressed quantitatively for a given duty cycle 81 as a function of the values of the targeted therapeutic efficacy 73 and the extent of potential side effects 74 at their point of intersection in the graph 70 of FIG. 5. The optimal therapeutic operating point 85 ("max") signifies a trade-off that occurs at the point of highest targeted therapeutic efficacy 73 in light of lowest potential side effects 74, and that point will typically be found within the range of a 5% to 30% duty cycle 81. Other expressions of duty cycles and related factors are possible.

Figure 7:
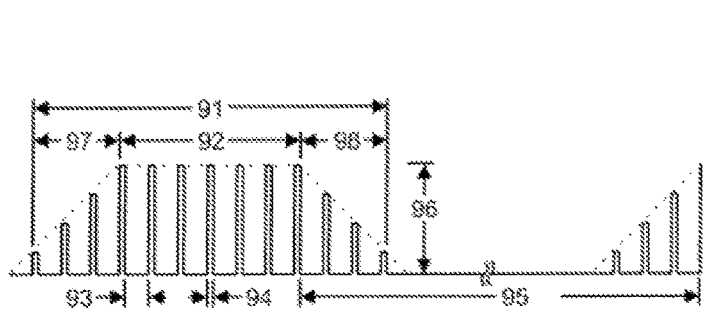
FIG. 7 is a timing diagram showing, by way of example, a stimulation cycle and an inhibition cycle of VNS as provided by implantable neurostimulator of FIG. 1.

Therapeutically and in the absence of patient physiology of possible medical concern, such as cardiac arrhythmias, VNS is delivered in a low-level maintenance dose that uses alternating cycles of stimuli application (ON) and stimuli inhibition (OFF) that are tuned to activate both afferent and efferent pathways. Stimulation results in parasympathetic activation and sympathetic inhibition, both through centrally mediated pathways and through efferent activation of preganglionic neurons and local circuit neurons. FIG. 7 is a timing diagram showing, by way of example, a stimulation cycle and an inhibition cycle of VNS 90, as provided by implantable neurostimulator 12 of FIG. 1. The stimulation parameters enable the electrical stimulation pulse output by the neurostimulator 12 to be varied by both amplitude (output current 96) and duration (pulse width 94). The number of output pulses delivered per second determines the signal frequency 93. In one embodiment, a pulse width in the range of 100 to 250 μSec delivers between 0.02 mA and 50 mA of output current at a signal frequency of about 10 Hz, although other therapeutic values could be used as appropriate. In general, the stimulation signal delivered to the patient may be defined by a stimulation parameter set comprising at least an amplitude, a frequency, a pulse width, and a duty cycle.

In one embodiment, the stimulation time is considered the time period during which the neurostimulator 12 is ON and delivering pulses of stimulation, and the OFF time is considered the time period occurring in-between stimulation times during which the neurostimulator 12 is OFF and inhibited from delivering stimulation.

In another embodiment, as shown in FIG. 7, the neurostimulator 12 implements a stimulation time 91 comprising an ON time 92, a ramp-up time 97, and a ramp-down time 98 that respectively precede and follow the ON time 92. Under this embodiment, the ON time 92 is considered to be a time during which the neurostimulator 12 is ON and delivering pulses of stimulation at the full output current 96. Under this embodiment, the OFF time 95 is considered to comprise the ramp-up time 97 and ramp-down time 98, which are used when the stimulation frequency is at least 10 Hz, although other minimum thresholds could be used, and both ramp-up and ramp-down times 97, 98 last two seconds, although other time periods could also be used. The ramp-up time 97 and ramp-down time 98 allow the strength of the output current 96 of each output pulse to be gradually increased and decreased, thereby avoiding deleterious reflex behavior due to sudden delivery or inhibition of stimulation at a programmed intensity.

Therapeutic vagus neural stimulation has been shown to provide cardioprotective effects. Although delivered in a maintenance dose having an intensity that is insufficient to elicit undesirable side effects, such as cardiac arrhythmias, ataxia, coughing, hoarseness, throat irritation, voice alteration, or dyspnea, therapeutic VNS can nevertheless potentially ameliorate pathological tachyarrhythmias in some patients. Although VNS has been shown to decrease defibrillation threshold, VNS has not been shown to terminate VF in the absence of defibrillation. VNS prolongs ventricular action potential duration, so may be effective in terminating VT. In addition, the effect of VNS on the AV node may be beneficial in patients with AF by slowing conduction to the ventricles and controlling ventricular rate.

Neural Fulcrum Zone

As described above, autonomic regulation therapy results in simultaneous creation of action potentials that simultaneously propagate away from the stimulation site in afferent and efferent directions within axons comprising the cervical vagus nerve complex. Upon stimulation of the cervical vagus nerve, action potentials propagate away from the stimulation site in two directions: efferently toward the heart and afferently toward the brain. Different parameter settings for the neurostimulator 12 may be adjusted to deliver varying stimulation intensities to the patient. The various stimulation parameter settings for current VNS devices include output current amplitude, signal frequency, pulse width, signal ON time, and signal OFF time.

When delivering neurostimulation therapies to patients, it is generally desirable to avoid stimulation intensities that result in either excessive tachycardia or excessive bradycardia. However, researchers have typically utilized the patient's heart rate changes as a functional response indicator or surrogate for effective recruitment of nerve fibers and engagement of the autonomic nervous system elements responsible for regulation of heart rate, which may be indicative of therapeutic levels of VNS. Some researchers have proposed that heart rate reduction caused by VNS stimulation is itself beneficial to the patient.

In accordance with embodiments of the present invention, a neural fulcrum zone is identified, and neurostimulation therapy is delivered within the neural fulcrum zone. This neural fulcrum zone corresponds to a combination of stimulation parameters at which autonomic engagement is achieved but for which a functional response determined by heart rate change is nullified due to the competing effects of afferently and efferently transmitted action potentials. In this way, the tachycardia-inducing stimulation effects are offset by the bradycardia-inducing effects, thereby minimizing side effects such as significant heart rate changes while providing a therapeutic level of stimulation. One method of identifying the neural fulcrum zone is by delivering a plurality of stimulation signals at a fixed frequency but with one or more other parameter settings changed so as to gradually increase the intensity of the stimulation.

Figure 8A:
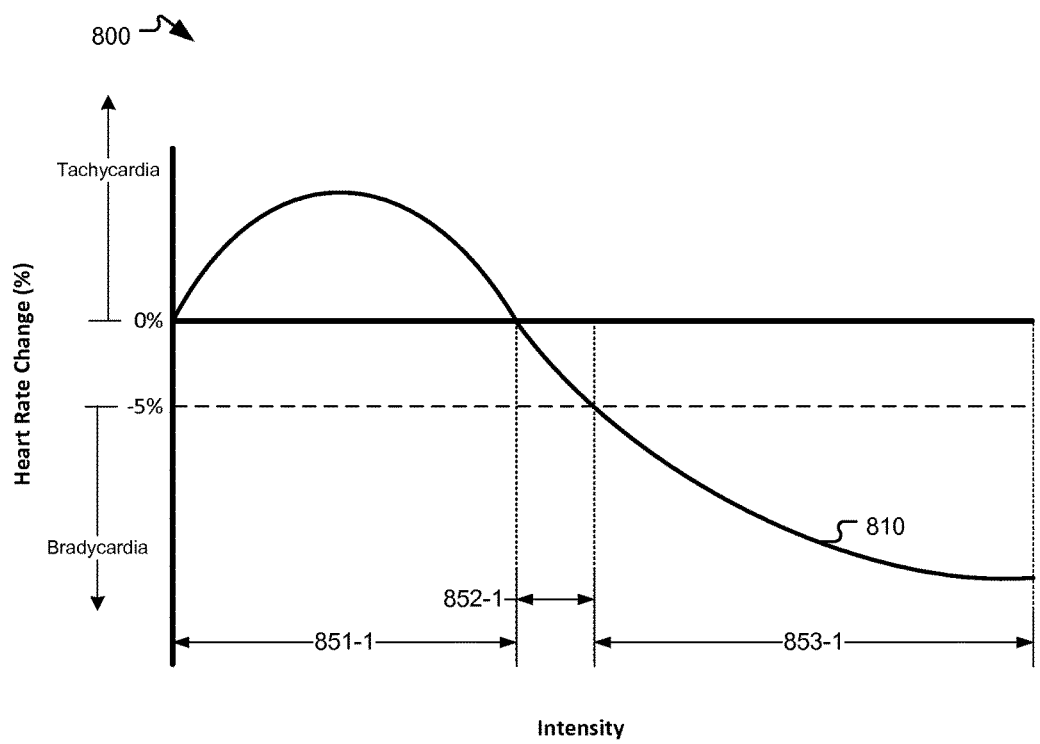
FIGS. 8A-8C are illustrative charts reflecting a heart rate response to gradually increased stimulation intensity at different frequencies.
Figure 8B:
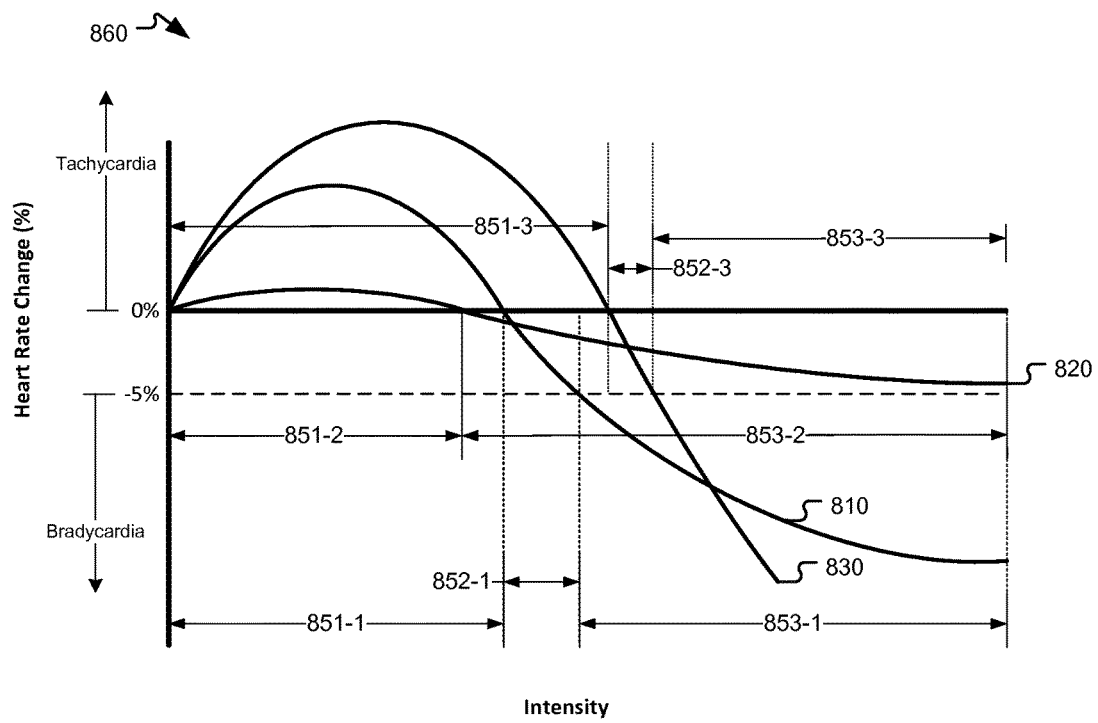
Figure 8C:
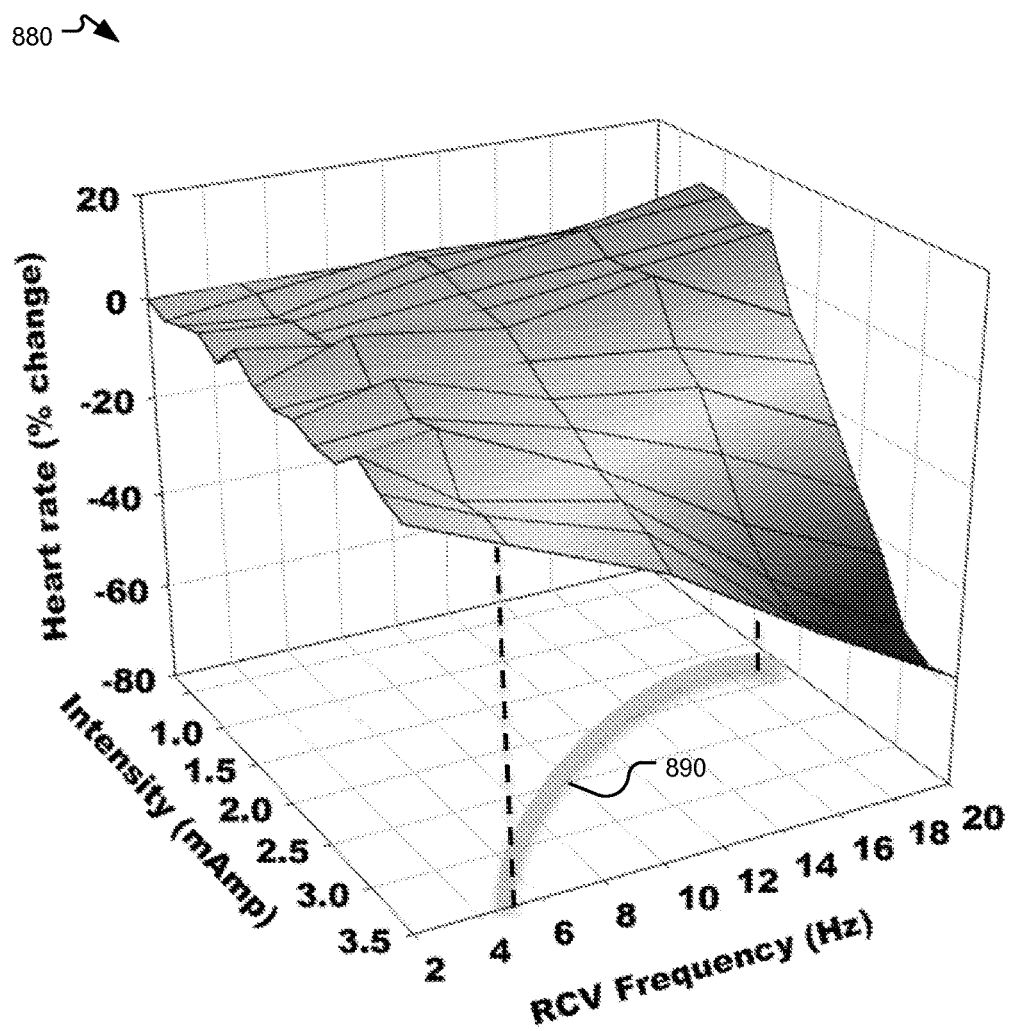

FIGS. 8A-8C provide illustrative charts reflecting the location of the neural fulcrum zone. FIG. 8A is a chart 800 illustrating a heart rate response in response to such a gradually increased intensity at a first frequency, in accordance with embodiments of the present invention. In this chart 800, the x-axis represents the intensity level of the stimulation signal, and the y-axis represents the observed heart rate change from the patient's baseline basal heart rate observed when no stimulation is delivered. In this example, the stimulation intensity is increased by increasing the output current amplitude.

A first set 810 of stimulation signals is delivered at a first frequency (e.g., 10 Hz). Initially, as the intensity (e.g., output current amplitude) is increased, a tachycardia zone 851-1 is observed, during which period, the patient experiences a mild tachycardia. As the intensity continues to be increased for subsequent stimulation signals, the patient's heart rate response begins to decrease and eventually enters a bradycardia zone 853-1, in which a bradycardia response is observed in response to the stimulation signals. As described above, the neural fulcrum zone is a range of stimulation parameters at which the functional effects from afferent activation are balanced with or nullified by the functional effects from efferent activation to avoid extreme heart rate changes while providing therapeutic levels of stimulation. In accordance with some embodiments, the neural fulcrum zone 852-1 can be located by identifying the zone in which the patient's response to stimulation produces either no heart rate change or a mildly decreased heart rate change (e.g., <5% decrease, or a target number of beats per minute). As the intensity of stimulation is further increased at the fixed first frequency, the patient enters an undesirable bradycardia zone 853-1. In these embodiments, the patient's heart rate response is used as an indicator of autonomic engagement. In other embodiments, other physiological responses may be used to indicate the zone of autonomic engagement at which the propagation of efferent and afferent action potentials are balanced, the neural fulcrum zone.

FIG. 8B is a chart 860 illustrating a heart rate response in response to such a gradually increased intensity at two additional frequencies, in accordance with embodiments of the present invention. In this chart 860, the x-axis and y-axis represent the intensity level of the stimulation signal and the observed heart rate change, respectively, as in FIG. 8A, and the first set 810 of stimulation signals from FIG. 8A is also shown.

A second set 810 of stimulation signals is delivered at a second frequency lower than the first frequency (e.g., 5 Hz). Initially, as the intensity (e.g., output current amplitude) is increased, a tachycardia zone 851-2 is observed, during which period, the patient experiences a mild tachycardia. As the intensity continues to be increased for subsequent stimulation signals, the patient's heart rate response begins to decrease and eventually enters a bradycardia zone 853-2, in which a bradycardia response is observed in response to the stimulation signals. The low frequency of the stimulation signal in the second set 820 of stimulation signals limits the functional effects of nerve fiber recruitment and, as a result, the heart response remains relatively limited. Although this low-frequency stimulation results in minimal side effects, the stimulation intensity is too low to result in effective recruitment of nerve fibers and engagement of the autonomic nervous system. As a result, a therapeutic level of stimulation is not delivered.

A third set 830 of stimulation signals is delivered at a third frequency higher than the first and second frequencies (e.g., 20 Hz). As with the first set 810 and second set 820, at lower intensities, the patient first experiences a tachycardia zone 851-3. At this higher frequency, the level of increased heart rate is undesirable. As the intensity is further increased, the heart rate decreases, similar to the decrease at the first and second frequencies but at a much higher rate. The patient first enters the neural fulcrum zone 852-3 and then the undesirable bradycardia zone 853-3. Because the slope of the curve for the third set 830 is much steeper than the second set 820, the region in which the patient's heart rate response is between 0% and −5% (e.g., the neural fulcrum zone 852-3) is much narrower than the neural fulcrum zone 852-2 for the second set 820. Accordingly, when testing different operational parameter settings for a patient by increasing the output current amplitude by incremental steps, it can be more difficult to locate a programmable output current amplitude that falls within the neural fulcrum zone 852-3. When the slope of the heart rate response curve is high, the resulting heart rate may overshoot the neural fulcrum zone and create a situation in which the functional response transitions from the tachycardia zone 851-3 to the undesirable bradycardia zone 853-3 in a single step. At that point, the clinician would need to reduce the amplitude by a smaller increment or reduce the stimulation frequency in order to produce the desired heart rate response for the neural fulcrum zone 852-3.

FIG. 8C is a chart 880 illustrating mean heart rate response surfaces in conscious, normal dogs during 14-second periods of right cervical vagus VNS stimulation ON-time. The heart rate responses shown in z-axis represent the percentage heart rate change from the baseline heart rate at various sets of VNS parameters, with the pulse width the pulse width set at 250 μSec, the pulse amplitude ranging from 0 mA to 3.5 mA (provided by the x-axis) and the pulse frequency ranging from 2 Hz to 20 Hz (provided by the y-axis). Curve 890 roughly represents the range of stimulation amplitude and frequency parameters at which a null response (i.e., 0% heart rate change from baseline) is produced. This null response curve 890 is characterized by the opposition of functional responses (e.g., tachycardia and bradycardia) arising from afferent and efferent activation.

Figure 9:
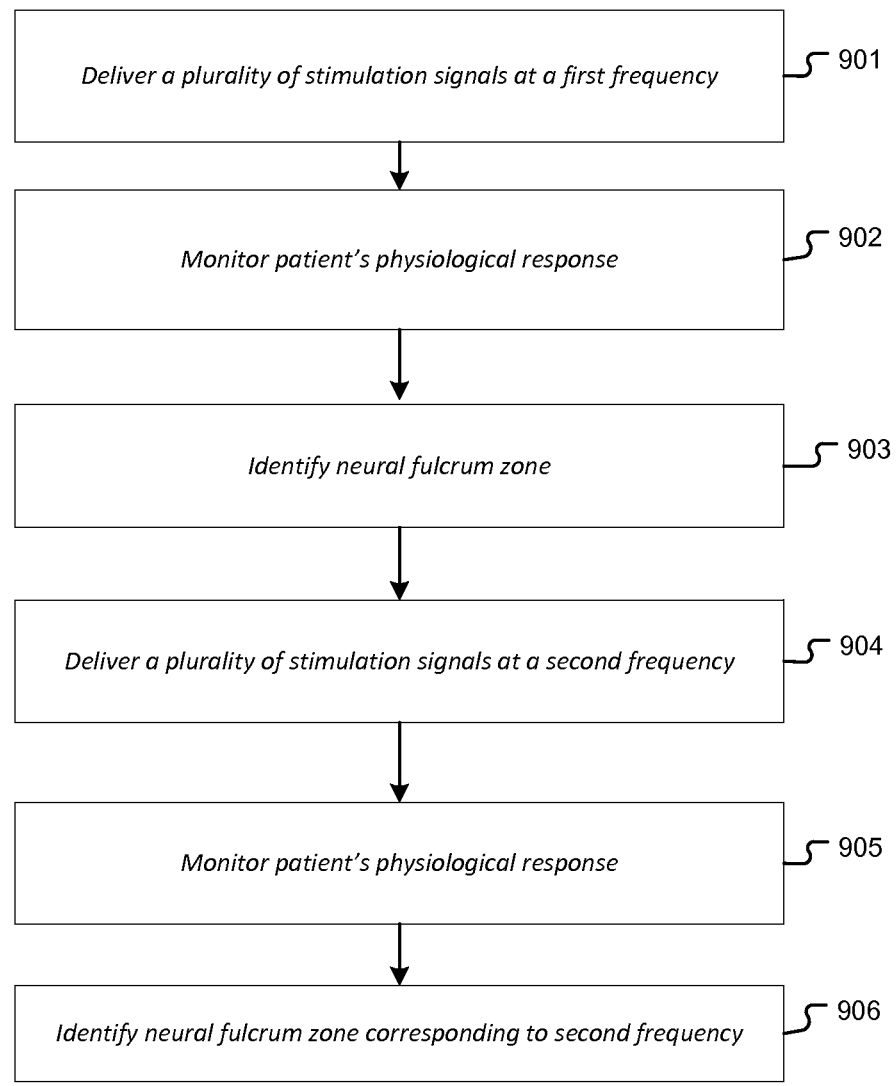
FIG. 9 illustrates a method of operating an implantable medical device comprising neurostimulator coupled to an electrode assembly.

FIG. 9 illustrates a method of operating an implantable medical device (IMD) comprising neurostimulator coupled to an electrode assembly. This method can be implemented using, for example, the VNS systems described above.

In step 901, the IMD is activated to deliver to the patient a plurality of stimulation signals at a first frequency (e.g., 2 Hz, as described above with respect to FIG. 9). Each of the plurality of stimulation signals is delivered having at least one operational parameter setting different than the other stimulation signals. For example, as described above, the output current amplitude is gradually increased while maintaining a fixed frequency. In other embodiments, different parameters may be adjusted to increase the intensity of stimulation at a fixed frequency.

In step 902, the patient's physiological response is monitored. In the example described above with respect to FIG. 8, the physiological response being observed is the patient's basal heart rate during stimulation at the various intensities at the first frequency. The physiological response may be measured using an implanted or external physiological sensor, such as, e.g., an implanted heart rate monitor 31, as well as other available physiological data, for instance, as derivable from an endocardial electrogram.

In step 903, the neural fulcrum zone for that first frequency is identified. In the example described above with respect to FIG. 8, the neural fulcrum zone corresponds to the range of stimulation parameter settings that result in a heart rate change of about 0% to about a decrease of 5%. In other embodiments, a different range of target heart rate changes or other physiological responses may be used to identify the neural fulcrum zone.

In accordance with some embodiments, stimulation at multiple frequencies may be delivered to the patient. In step 904, the IMD is activated to deliver to the patient a plurality of stimulation signals at a second frequency. In step 905, the patient's physiological response (e.g., basal heart rate) at the second frequency is observed. In step 906, the neural fulcrum zone for the second frequency is identified. Additional frequencies may be delivered, and corresponding neural fulcrum zones may be identified for those frequencies.

As described in the various embodiments above, neural fulcrum zones may be identified for a patient. Different neural fulcrum zones may be identified using different stimulation signal characteristics. Based on the signal characteristics, the patient's physiological response to the stimulation may be mild with a low slope, as with, for example, the first set of stimulation signals 810 at a low frequency, or may be extreme with a large slope, as with, for example, the third set of stimulation signals 830 at a high frequency. Accordingly, it may be advantageous to identify a frequency at which the reaction is moderate, producing a moderate slope corresponding to a wide neural fulcrum zone in which therapeutically effective stimulation may be provided to the patient.

The observation of tachycardia in the tachycardia zone 851-2 and bradycardia in the bradycardia zone 853-2 indicates that the stimulation is engaging the autonomic nervous system, which suggests that a therapeutically effective intensity is being delivered. Typically, clinicians have assumed that stimulation must be delivered at intensity levels where a significant physiological response is detected. However, by selecting an operational parameter set in the neural fulcrum zone 852-2 that lies between the tachycardia 851-2 and the bradycardia zone 853-2, the autonomic nervous system may still be engaged without risking the undesirable effects of either excessive tachycardia or excessive bradycardia. At certain low frequencies, the bradycardia zone may not be present, in which case the neural fulcrum zone 852-2 is located adjacent to the tachycardia zone. While providing stimulation in the neural fulcrum zone, the autonomic nervous system remains engaged, but the functional effects of afferent and efferent activation are sufficiently balanced so that the heart rate response is nullified or minimized (<5% change). Ongoing stimulation therapy may then be delivered to the patient at a fixed intensity within the neural fulcrum zone.

Fine Control of Neurostimulation

In accordance with embodiments of the present invention, fine control of neurostimulation intensity settings may be achieved for locating the neural fulcrum zone. A patient's physiological response to stimulation may vary depending on stimulation frequency and other stimulation parameters, and may be monitored by a clinician as a parameter indicative of the patient's autonomic balance. In accordance with embodiments of the present invention, one physiological response indicative of autonomic balance is a heart rate response.

In the embodiment shown in FIG. 8B, the patient's varying heart rate response to stimulation at different stimulation frequencies is shown. At low stimulation frequencies, such as the 5 Hz frequency corresponding to the second set 820 of stimulation signals in FIG. 8B, the slope of the heart rate response curve is very low, and a step change in stimulation intensity results in a small change in cardiac response. In contrast, at high stimulation frequencies, such as the 20 Hz frequency corresponding to the third set 830 of stimulation signals in FIG. 8B, the slope of the heart rate response curve is large, particularly in the neural fulcrum zone 852-3, and a step change in stimulation intensity results in a large change in cardiac response. In accordance with embodiments of the present invention, an understanding of the relationship between the neural fulcrum zone and the stimulation parameters may be used to enable fine control of intensity settings when attempting to locate the neural fulcrum zone.

Figure 10:
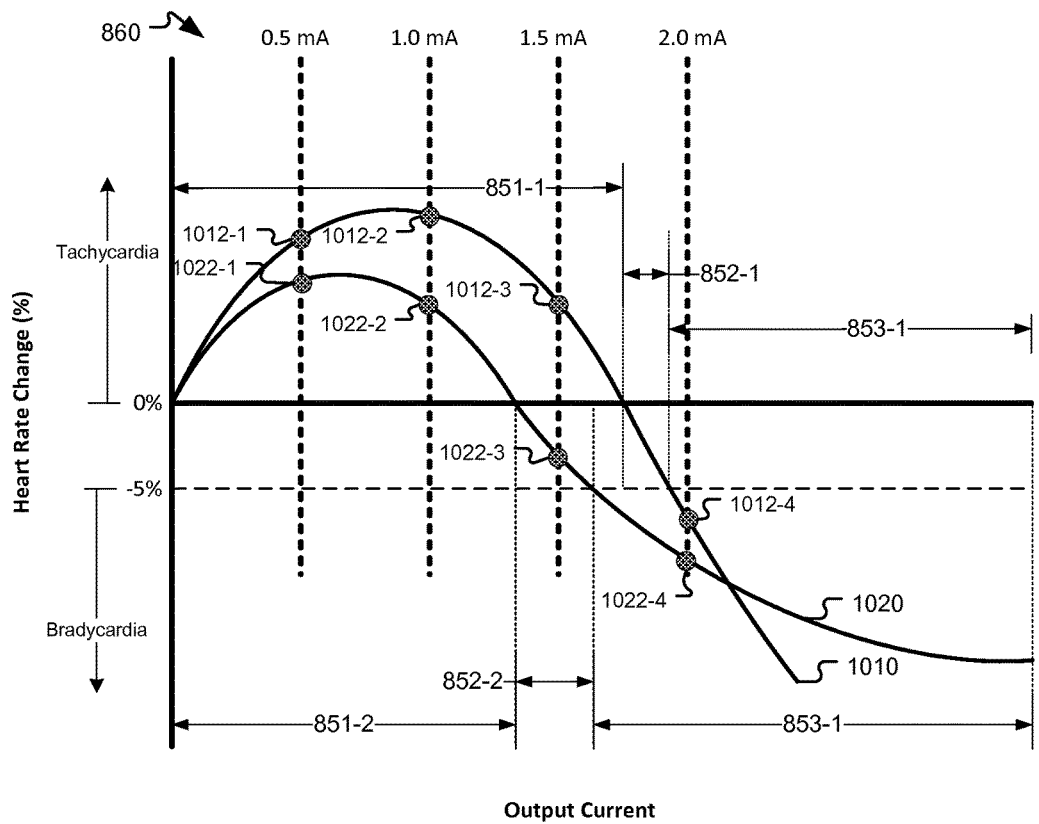
FIG. 10 is an illustrative chart reflecting a heart rate response to gradually increased stimulation intensity delivered by an implanted VNS system at two different frequencies.

FIG. 10 is an illustrative chart reflecting a heart rate response to gradually increased stimulation intensity delivered by an implanted VNS system at two different frequencies. In this simplified example, the intensity setting along the x-axis comprises the stimulation output current, a first set 1010 of stimulation signals is delivered at a first frequency (e.g., 20 Hz), and a second set 1020 of stimulation signals is delivered at a second frequency (e.g., 10 Hz).

In various embodiments, the various stimulation parameter settings for the VNS system are adjusted according to predefined increments. In the example shown in FIG. 10, adjustments to the stimulation output current are made in 0.5 mA increments. In other cases, the adjustments to the stimulation output current may be made in different increments, such as, for example, 0.25 mA or 1.0 mA. In some cases, these predefined increments may be dictated by hardware or software limitations, such as a VNS pulse generator that can only be adjusted in 0.5 mA increments. In other cases, the predefined increments may be imposed by the manufacturer or the clinician to improve consistency, simplicity, or administrative ease.

If the VNS system were used to deliver a continuous range of output currents at the first and second frequencies, the continuous heart rate response curves 1010 and 1020 shown in FIG. 10 would be detected. However, in accordance with embodiments of the present invention, the VNS system is configured to deliver stimulation output currents at predetermined increments of 0.5 mA. As a result, when a first set 1010 of stimulation signals is delivered at 20 Hz, four points along the heart rate response curve are detected: 1012-1, 1012-2, 1012-3, and 1012-4. The heart rate responses at 1012-1, 1012-2, and 1012-3 detected at the first three current levels (0.5 mA, 1.0 mA, and 1.5 mA) all fall within the tachycardia zone 851-1 for the first frequency. When the output current is increased by the predetermined increment of 0.5 mA, the next detected heart rate response at 1012-4 falls in the bradycardia zone 853-1. Because of the steep slope of the heart rate response curve in the neural fulcrum zone 852-1, when increasing the output current by the predefined 0.5 mA increment, a heart rate response in the neural fulcrum zone 852-2 is not detected.

When attempting to locate the neural fulcrum for a particular patient, if the detected heart rate response transitions from the tachycardia zone 851-1 to the bradycardia zone 853-1 in response to a single increment increase of the intensity setting, it may be desirable to use a different stimulation frequency to locate the neural fulcrum. Accordingly, the stimulation frequency is decreased (e.g., to 10 Hz, as shown in FIG. 10), and a second set 1020 of stimulation signals are delivered to the patient at the lower frequency. As with the first set 1010, the intensity of the stimulation is increased by predefined increments (e.g., of 0.5 mA) to provide heart rate response points 1022-1, 1022-2, 1022-3, and 1022-4. Unlike the first set 1010, the heart rate response curve for the second frequency has a lower slope, which provides a clinician with a finer resolution investigation of the heart rate response curve in the neural fulcrum zone 852-2, even when limited by the same 0.5 mA predefined increment of output current. As shown in FIG. 10, the first two stimulation signals at 0.5 mA and 1.0 mA result in heart rate response points 1022-1 and 1022-2, respectively, which fall within the tachycardia zone 851-2. Increasing the output current to 1.5 mA results in heart rate response point 1022-3, which falls squarely within the neural fulcrum zone 852-2. If the output current is increased by another predefined increment to 2.0 mA, a heart rate response point 1022-4 falling within the bradycardia zone 853-1 is detected.

As a result, a clinician may determine that the stimulation parameter settings resulting in the heart rate response point 1022-3 correspond to the neural fulcrum zone. Accordingly, the VNS system may be configured to chronically deliver stimulation signals corresponding to the identified neural fulcrum zone to treat chronic cardiac dysfunction.

In some situations, such as that illustrated in the second set 820 of stimulation signals of FIG. 8B, the stimulation frequency may be so low that stimulation signal limits the functional effects of nerve fiber recruitment, and the heart rate response remains relatively limited. Although this low frequency stimulation results in minimal side effects and never induces bradycardia, despite increases in the output current, the overall stimulation intensity remains too low to result in effective recruitment of nerve fibers and engagement of the autonomic nervous system. As a result, a therapeutic level of stimulation is not delivered. This is illustrated in FIG. 8B by the low slope of the heart rate response to the second set 820 of stimulation signals. Despite increases in the output current up to maximum levels tolerable by the patient, the stimulation signals never reach the level of autonomic engagement.

In accordance with embodiments of the present invention, if incremental increases of an intensity setting (e.g., output current) at a first frequency do not result in an adequate change in the heart rate, the frequency of stimulation may be increased to produce a heart rate response curve with a larger slope. The output current may be reduced to an initial level (e.g., 0.5 mA), with subsequent stimulation signals delivered at incrementally increasing output currents. After transitioning past the tachycardia zone, a stimulation signal delivered at the higher frequency at one output current level will induce a heart rate response point that falls within the neural fulcrum zone, and a subsequent stimulation signal with a single predefined incremental increase in the output current level induces a heart rate response in the bradycardia zone.

The output current level may then be reduced by the predefined increment to bring the stimulation back into the neural fulcrum zone.

Dynamic Stimulation Adjustment

In some embodiments described herein, the stimulation parameters may be manually adjusted by a clinician in order to locate the neural fulcrum zone. In accordance with other embodiments of the present invention, computer-implemented methods are used for monitoring the patient's response to stimulation and dynamically adjusting stimulation parameters in order to locate the neural fulcrum zone. This monitoring and dynamic adjustment may be performed in clinic utilizing an external control system, or it may be automatically performed by an implanted control system coupled to an implanted physiological sensor, such as, for example, an ECG sensor for monitoring heart rate.

Figure 11A:
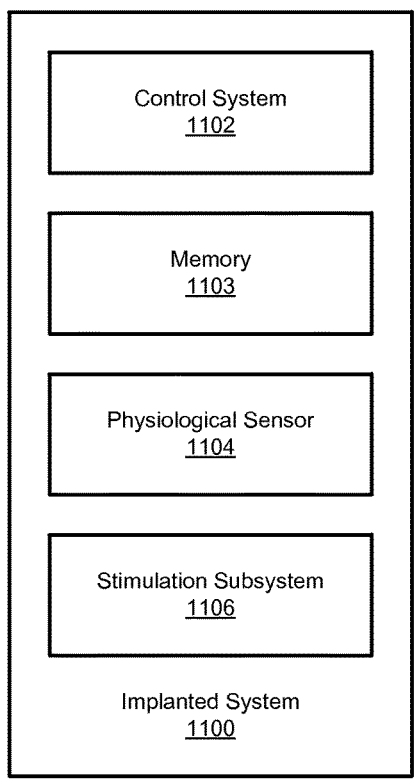
FIGS. 11A-11B are block diagrams of neurostimulation systems in accordance with embodiments of the present invention.

FIG. 11A is a simplified block diagram of an implanted neurostimulation system 1100 in accordance with embodiments of the present invention. The implanted neurostimulation system 1100 comprises a control system 1102 comprising a processor programmed to operate the system 1100, a memory 1103, a physiological sensor 1104, and a stimulation subsystem 1106. The physiological sensor 1104 may be configured to monitor any of a variety of patient physiological signals, and the stimulation subsystem 1106 may be configured to deliver a stimulation signal to the patient. In one example, the physiological sensor 1104 comprises an ECG sensor for monitoring heart rate, and the stimulation subsystem 1106 comprises a neurostimulator 12 programmed to deliver ON-OFF cycles of stimulation to the patient's vagus nerve.

The control system 1102 is programmed to activate the neurostimulator 12 to deliver varying stimulation intensities to the patient and to monitor the physiological signals in response to those stimulation signals.

Figure 12:
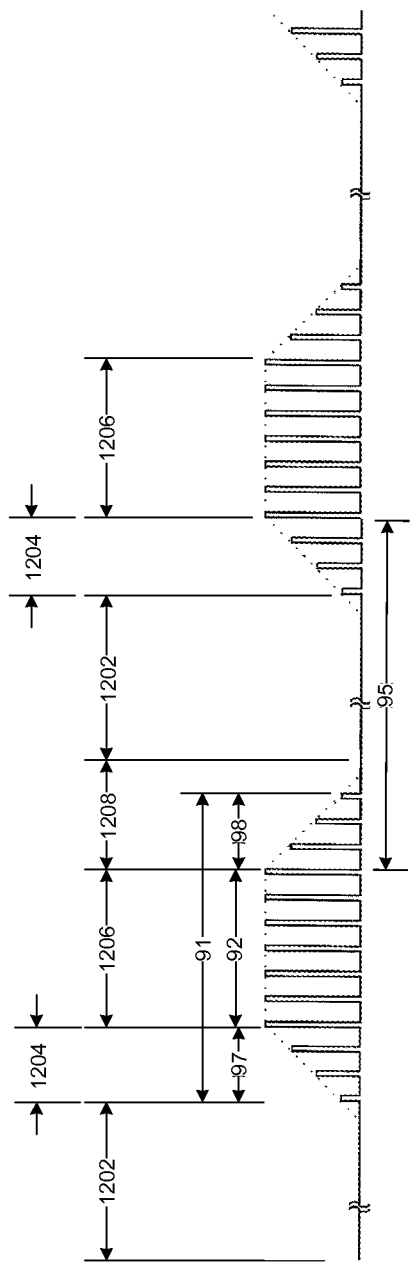
FIG. 12 is an illustrative graph indicating monitoring periods during delivery of stimulation signals in accordance with embodiments of the present invention.

FIG. 12 is an illustrative graph indicating monitoring periods during delivery of stimulation signals in accordance with embodiments of the present invention. First, the control system 1102 activates the physiological sensor 1104 to monitor the patient's heart rate (or other physiological signal) during a resting period 1202 in which the neurostimulator 12 is in an OFF time period with no stimulation signals being delivered to the patient. The monitoring heart rate during the resting period 1202 establishes the patient's baseline heart rate.

Next, during the stimulation ON time period 92, the control system 1102 activates the physiological sensor 1104 to monitor the patient's heart rate response to the stimulation during a response period 1206. As described above, the heart rate response during stimulation can be used to locate the neural fulcrum zone. For example, if tachycardia is detected, the control system 1102 may be configured to automatically increase the intensity of subsequent stimulation signals in order to travel farther along the response curve described above with respect to FIG. 8B. The control system 1102 may be further programmed to gradually increase the stimulation intensity until bradycardia is detected and the neural fulcrum is located.

In accordance with some embodiments, the control system 1102 may be programmed to maintain a stimulation parameter setting for a plurality of cycles, while monitoring the baseline heart rate and heart rate response for each stimulation cycle. The control system 1102 may be programmed to calculate one or more statistical descriptors (e.g., mean, median, minimum, maximum, etc.) of the baseline heart rates and heart rate responses in order to provide a more accurate measurement of the patient's response to stimulation by aggregating the multiple responses to stimulation. In addition, the control system 1102 may store the physiological measurements in the memory 1103 for performing these calculations for later analysis.

In accordance with some embodiments, the control system 1102 may be programmed to utilize a delay period 1208 following completion of an ON time period prior to monitoring the baseline heart rate during resting period 1202. This delay period 1208 may comprise, for example, between one and five seconds, or more, and may provide the patient's heart with a period of time to return to its baseline heart rate before resuming monitoring. In accordance with some embodiments, the control system 1102 may be programmed to utilize an ON time delay period (not shown) following initiation of an ON time period prior to monitoring the heart rate response during the response period 1206. This ON time delay period may comprise, for example, between one and five seconds, or more, and may provide the patient's heart with a period of time to adjust from the baseline rate and stabilize at the stimulation response rate before initiating monitoring during the response period 1206. In some embodiments, the physiological sensor 1104 may continuously monitor the patient's heart rate (or other physiological signal), and the control system 1102 is programmed to locate the heart rate during the particular periods of interest (e.g., resting period 1202 and response period 1206).

Figure 11B:
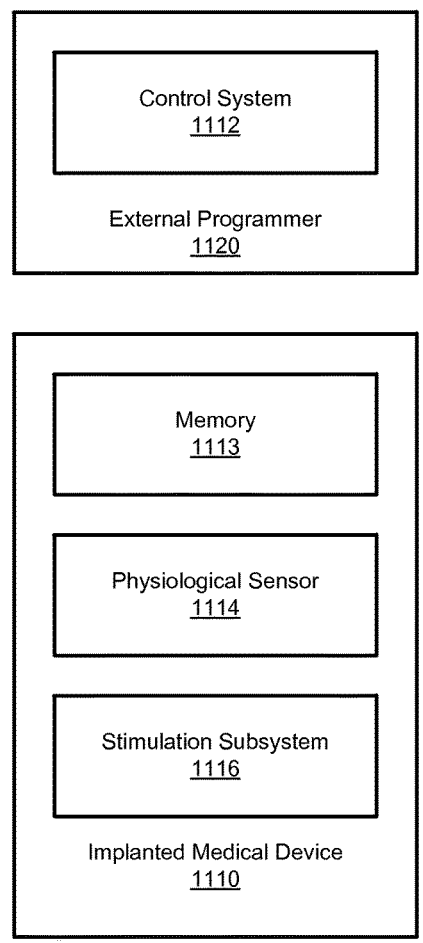

The synchronization of the stimulation signal delivery and the monitoring of the patient's heart rate may be advantageously implemented using control system in communication with both the stimulation subsystem 1106 and the physiological sensor 1104, such as by incorporating all of these components into a single implantable device. In accordance with other embodiments, the control system may be implemented in a separate implanted device or in an external programmer 1120, as shown in FIG. 11B. The external programmer 1120 in FIG. 11B may be utilized by a clinician or by the patient for adjusting stimulation parameters. The external programmer 1120 is in wireless communication with the implanted medical device 1110, which includes the stimulation subsystem 1116. In the illustrated embodiment, the physiological sensor 1114 is incorporated into the implanted medical device 1110, but in other embodiments, the sensor 1114 may be incorporated into a separate implanted device, may be provided externally and in communication with the external programmer 1120, or may be provided as part of the external programmer 1120.

Long-Term Monitoring

In accordance with embodiments of the present invention, the implanted device includes a physiological sensor configured to acquire a physiological signal from the patient and a non-volatile memory for recording the physiological signals over extended periods of time on an ambulatory basis. In some embodiments, the physiological sensor comprises a heart rate sensor for measuring heart rate variability. This can permit the device to deliver neurostimulation signals to the patient on a chronic basis, while recording the patient's physiological response to the stimulation outside of the clinic over extended periods of time. The physiological signals may be recorded over periods of time such as, for example, days, weeks, months, or years. The recording of the physiological signals may be continuous (e.g., 24 hours per day, 7 days a week), or may be intermittent. In systems where the monitoring and recording is intermittent, the recording may be performed for any desired length of time (e.g., minutes, hours, etc.) and at any desired periodicity (e.g., during certain periods of the day, once per hour, day, week, month, or other period of interest).

The implanted device may include a communication interface for wirelessly transmitting the recorded physiological signals to an external computing device, such as the external programmer described above. The recorded signals can then be analyzed, evaluated, or otherwise reviewed by a clinician. As a result, the clinician can set the stimulation parameters for the patient's implanted device, and then can review the patient's response to chronic stimulation at that parameter setting over extended periods of time. The extended ambulatory data can permit the clinician to adjust or refine the stimulation parameters to achieve the optical therapeutic effect, without being limited to the physiological signals of short duration recorded in clinic.

Closed-Loop Neurostimulation

As described above, embodiments of the implanted device may include a physiological sensor, such as a heart rate sensor, configured to monitor a physiological signal from the patient over extended periods of time on an ambulatory basis. In accordance with embodiments of the present invention, the implanted device may be configured to adjust stimulation parameters to maintain stimulation in the neural fulcrum zone based on detected changes in the physiological response to stimulation.

In some embodiments described above, the identification of the neural fulcrum zone and the programming of the stimulation parameters to deliver stimulation signals in the neural fulcrum zone may be performed in a clinic by a healthcare provider. In some embodiments, the implanted medical device may be configured to automatically monitor the patient's physiological response using an implanted physiological sensor to initially identify the neural fulcrum zone and set the stimulation parameters to deliver signals in the neural fulcrum zone. In addition, under certain circumstances, the patient's physiological response to those initial stimulation parameters may change. This change could occur as the stimulation is chronically delivered over an extended period of time as the patient's body adjusts to the stimulation. Alternatively, this change could occur as a result of other changes in the patient's condition, such as changes in the patient's medication, disease state, circadian rhythms, or other physiological change.

If the changes in the patient's response to stimulation results in a change in the patient's response curve, the initially identified stimulation parameters may no longer deliver stimulation in the neural fulcrum zone. Therefore, it may be desirable for the implanted medical device to automatically adjust one or more stimulation parameters (e.g., pulse amplitude) so that subsequent stimulation signals may be delivered in the neural fulcrum zone. For example, in embodiments described above, where the monitored physiological response is the patient's heart rate, then if tachycardia is later detected in response to stimulation signals that had previously resulted in a transition heart rate response, the IMD may be configured to automatically increase the pulse amplitude (or other stimulation parameters) until a transition heart rate response is again detected. Subsequent stimulation may continue to be delivered using the new stimulation parameters until another change in the patient's physiological response is detected.

In some embodiments, the patients physiological response may be substantially continuously monitored. In other embodiments, the patient's physiological response may be monitored on a periodic basis, such as, for example, every minute, hour, day, or other periodic or aperiodic schedule that may be desired in order to provide the desired monitoring schedule. In other embodiments, the patient's physiological response may be monitored in response to a control signal delivered by an external device, such as a control magnet or wireless data signal from a programming wand. The external control signal to initiate monitoring may be delivered when it is desired to monitor the physiological response when a patient condition is changing, such as when the patient is about to take a medication, is about to go to sleep, or has just wakened. In some embodiments, the external control signal may be used by the patient when an automatically increasing stimulation intensity in response to monitoring physiological signals is causing undesirable side effects. When the IMD receives such a control signal, the IMD may be programmed to automatically reduce the stimulation intensity until the side effects are alleviated (as indicated, for example, by a subsequent control input).

It will be understood that output current is merely one example of a stimulation parameter that may be adjusted in order to identify the neural fulcrum zone. In other embodiments, the stimulation may be varied by adjusting the other intensity parameters, such as, for example, pulse width, pulse frequency, and duty cycle.

In various embodiments described above, the patient's heart rate response is used as the patient parameter indicative of the patient's autonomic regulatory function in response to the stimulation for locating the neural fulcrum zone. In other embodiments, different patient parameters may be monitored in conjunction with stimulation, including, for example, other heart rate variability parameters, ECG parameters such as PR interval and QT interval, and non-cardiac parameters such as respiratory rate, pupil diameter, and skin conductance. Increases and decreases in these patient parameters in response to changes in stimulation intensity may be used to identify the patient's neural fulcrum. If the change in the patient parameter in response to an incremental increase in a stimulation parameter is too large to enable identification of the neural fulcrum zone (e.g., the slope of the response curve is large), the frequency of the stimulation may be decreased and an additional set of stimulation signals may be delivered to the patient. At the lower frequency, the slope of the response curve will decrease, enabling a finer resolution identification of the neural fulcrum zone. Conversely, if the change in the patient parameter is too low (e.g., the slope of the response curve is too small), the frequency may be increased in order to achieve finer resolution identification of the neural fulcrum zone.

While the invention has been particularly shown and described as referenced to the embodiments thereof, those skilled in the art will understand that the foregoing and other changes in form and detail may be made therein without departing from the spirit and scope. For example, in various embodiments described above, the stimulation is applied to the vagus nerve. Alternatively, spinal cord stimulation (SCS) may be used in place of or in addition to vagus nerve stimulation for the above-described therapies. SCS may utilize stimulating electrodes implanted in the epidural space, an electrical pulse generator implanted in the lower abdominal area or gluteal region, and conducting wires coupling the stimulating electrodes to the generator.

What is claimed is:
1. A neurostimulation system, comprising:
an electrode assembly; and
a neurostimulator coupled to the electrode assembly, the neurostimulator comprising:
a control circuit; and a memory operably coupled to the control circuit and comprising instructions that, when executed by the control circuit, cause the control circuit to:

deliver stimulation pulses via the electrode assembly using a first set of stimulation parameters to cause a heart rate response in a neural fulcrum zone, the neural fulcrum zone being defined by a heart rate reduction between a baseline heart rate and a predefined threshold;

detect whether the heart rate response caused by the first set of stimulation parameters has deviated from the neural fulcrum zone by comparing the heart rate response to the baseline heart rate and the predefined threshold detecting whether the heart rate response has deviated from the neural fulcrum zone comprising detecting that the heart rate response has deviated from the neural fulcrum zone in response to detecting either a heart rate reduction of greater than the predefined threshold or a heart rate at or above the baseline heart rate;

continue to deliver the stimulation pulses using the first set of stimulation parameters in response to detecting the heart rate response remains within the neural fulcrum zone; and deliver the stimulation pulses using a second set of stimulation parameters in response to determining the heart rate response has deviated from the neural fulcrum zone, the stimulation pulses using second set of parameters configured to modify the heart rate response back to the neural fulcrum zone.

2. The neurostimulation system according to claim 1, wherein in response to detecting tachycardia, the control circuit sets the second set of stimulation parameters to include a first stimulation intensity greater than a second stimulation intensity of the first set of stimulation parameters, and in response to detecting bradycardia, the control circuit sets the second set of stimulation parameters to include a third stimulation intensity less than the second stimulation intensity of the first set of stimulation parameters.

3. The neurostimulation system according to claim 1, wherein the control circuit continuously detects whether the heart rate response caused by the first set of stimulation parameters has deviated from the neural fulcrum zone.

4. The neurostimulation system according to claim 1, wherein the control circuit periodically detects whether the heart rate response caused by the first set of stimulation parameters has deviated from the neural fulcrum zone.

5. The neurostimulation system according to claim 1, wherein the control circuit detects whether the heart rate response caused by the first set of stimulation parameters has deviated from the neural fulcrum zone in response to a control input.

6. The neurostimulation system according to claim 5, wherein said control input comprises an input from at least one of a programmer or a magnet.

7. The neurostimulation system according to claim 5, wherein the control circuit sets the second set of stimulation parameters to include a first stimulation intensity less than a second stimulation intensity of the first set of stimulation parameters in response to receiving the control input.

8. The neurostimulation system according to claim 1, wherein the second set of stimulation parameters have a first stimulation intensity and the first set of stimulation parameters have a second stimulation intensity, wherein the stimulation intensity is defined by at least one of a pulse width, a pulse frequency, an output current or a duty cycle.

9. A neurostimulator comprising:
a control circuit; and
a memory operably coupled to the control circuit and comprising instructions that, when executed by the control circuit, cause the control circuit to:

deliver stimulation pulses using a first set of stimulation parameters to cause a heart rate response in a neural fulcrum zone, the neural fulcrum zone being defined by a heart rate reduction between a baseline heart rate and a predefined threshold;

detect whether the heart rate response caused by the first set of stimulation parameters has deviated from the neural fulcrum zone by comparing the heart rate response to the baseline heart rate and the predefined threshold, detecting whether the heart rate response has deviated from the neural fulcrum zone comprising detecting that the heart rate response has deviated from the neural fulcrum zone in response to detecting either a heart rate reduction of greater than the predefined threshold or a heart rate at or above the baseline heart rate;

continue to deliver the stimulation pulses using the first set of stimulation parameters in response to detecting the heart rate response remains within the neural fulcrum zone; and deliver the stimulation pulses using a second set of stimulation parameters in response to determining the heart rate response has deviated from the neural fulcrum zone, the stimulation pulses using second set of parameters configured to modify the heart rate response back to the neural fulcrum zone.

10. The neurostimulator according to claim 9, wherein in response to detecting tachycardia, the control circuit sets the second set of stimulation parameters to include a first stimulation intensity greater than a second stimulation intensity of the first set of stimulation parameters, and in response to detecting bradycardia, the control circuit sets the second set of stimulation parameters to include a third stimulation intensity less than the second stimulation intensity of the first set of stimulation parameters.

11. The neurostimulator according to claim 9, wherein the control circuit continuously detects whether the heart rate response caused by the first set of stimulation parameters has deviated from the neural fulcrum zone.

12. The neurostimulator according to claim 9, wherein the control circuit periodically detects whether the heart rate response caused by the first set of stimulation parameters has deviated from the neural fulcrum zone.

13. The neurostimulator according to claim 9, wherein the control circuit detects whether the heart rate response caused by the first set of stimulation parameters has deviated from the neural fulcrum zone in response to a control input.

14. The neurostimulator according to claim 13, wherein said control input comprises an input from at least one of a programmer or a magnet.

15. The neurostimulator according to claim 13, wherein the control circuit sets the second set of stimulation parameters to include a first stimulation intensity less than a second stimulation intensity of the first set of stimulation parameters in response to receiving the control input.

16. A method of delivering neurostimulation, the method comprising:
delivering stimulation pulses using a first set of stimulation parameters to cause a heart rate response in a neural fulcrum zone, the neural fulcrum zone being defined by a heart rate reduction between a baseline heart rate and a predefined threshold;

detecting whether the heart rate response caused by the first set of stimulation parameters has deviated from the neural fulcrum zone by comparing the heart rate response to the baseline heart rate and the predefined threshold, detecting whether the heart rate response has deviated from the neural fulcrum zone comprising detecting that the heart rate response has deviated from the neural fulcrum zone in response to detecting either a heart rate reduction of greater than the predefined threshold or a heart rate at or above the baseline heart rate;

continuing to deliver the stimulation pulses using the first set of stimulation parameters in response to detecting the heart rate response remains within the neural fulcrum zone; and delivering the stimulation pulses using a second set of stimulation parameters in response to determining the heart rate response has deviated from the neural fulcrum zone, the stimulation pulses using second set of parameters configured to modify the heart rate response back to the neural fulcrum zone.

17. The method according to claim 16, wherein delivering the stimulation pulses using the second set of stimulation parameters comprises, in response to detecting tachycardia, setting the second set of stimulation parameters to include a first stimulation intensity greater than a second stimulation intensity of the first set of stimulation parameters and, in response to detecting bradycardia, setting the second set of stimulation parameters to include a third stimulation intensity less than the second stimulation intensity of the first set of stimulation parameters.

18. The method according to claim 16, wherein detecting whether the heart rate response caused by the first set of stimulation parameters has deviated from the neural fulcrum zone occurs in response to a control input.

19. The method according to claim 18, wherein the control input comprises an input from at least one of a programmer or a magnet.

20. The method according to claim 18, wherein delivering the stimulation pulses using the second set of stimulation parameters comprises setting the second set of stimulation parameters to include a first stimulation intensity less than a second stimulation intensity of the first set of stimulation parameters in response to receiving the control input.

* * * * *